(12) United States Patent
Blundell et al.

(10) Patent No.: US 7,476,740 B2
(45) Date of Patent: Jan. 13, 2009

(54) TROPANE COMPOUNDS

(75) Inventors: Paul Blundell, Winchester, MA (US);
Peter C. Meltzer, Lexington, MA (US);
Bertha K. Madras, Newton, MA (US)

(73) Assignees: President and Fellows of Harvard College, Cambridge, MA (US);
Organix, Inc., Woburn, MA (US)

( * ) Notice: Subject to any disclaimer, the term of this patent is extended or adjusted under 35 U.S.C. 154(b) by 252 days.

(21) Appl. No.: 10/400,825

(22) Filed: Mar. 27, 2003

(65) Prior Publication Data

US 2003/0232819 A1  Dec. 18, 2003

Related U.S. Application Data

(60) Provisional application No. 60/368,382, filed on Mar. 28, 2002, provisional application No. 60/375,505, filed on Apr. 25, 2002.

(51) Int. Cl.
*C07C 255/00* (2006.01)
*C07C 259/00* (2006.01)
*C07C 249/00* (2006.01)
*C07C 251/00* (2006.01)
*C07C 291/00* (2006.01)
*C07D 451/02* (2006.01)

(52) U.S. Cl. .................................... 546/124; 558/446
(58) Field of Classification Search ............... 558/446; 546/124; 514/124

See application file for complete search history.

(56) References Cited

U.S. PATENT DOCUMENTS

| | | | | |
|---|---|---|---|---|
| 5,374,636 A | * | 12/1994 | Moldt et al. | 514/304 |
| 5,493,026 A | | 2/1996 | Elmaleh et al. | 346/132 |
| 5,736,556 A | | 4/1998 | Moldt et al. | 514/304 |
| 5,770,180 A | | 6/1998 | Madras et al. | 424/1.81 |
| 5,948,933 A | * | 9/1999 | Meltzer et al. | 558/426 |

OTHER PUBLICATIONS

The International Search Report dated May 27, 2004, issued in corresponding International Application No. PCT/US03/09432.

* cited by examiner

*Primary Examiner*—San-ming Hui
(74) *Attorney, Agent, or Firm*—Edwarsds Angell Palmer & Dodge LLP; George W. Neuser; Mark D. Russett

(57) ABSTRACT

The present invention provides novel tropane compounds and methods for their use.

7 Claims, 9 Drawing Sheets

14

15

16

17

24

25

26

27

TROPANE COMPOUNDS

RELATED APPLICATION(S)

This application claims priority to U.S. Provisional Patent Application Ser. No. 60/368,382, filed Mar. 28, 2002, and U.S. Provisional Patent Application Ser. No. 60/375,505, filed Apr. 25, 2002, the entire teachings of which are incorporated herein by reference.

STATEMENT OF GOVERNMENT SUPPORT

This invention is supported by NIDA Grant No. NO1 DA 1-8825 and the government has certain rights to the invention.

FIELD OF THE INVENTION

The present invention relates to novel tropane compounds that have an affinity for a monoamine transporter, e.g., the dopamine transporter (DAT), serotonin transporter (SET) or norepinephrine transporter (NET). Such agents can be useful for the early diagnosis and treatment of diverse neurological and psychiatric conditions.

BACKGROUND OF THE INVENTION

Monoamine transporters play a variety of roles, and compounds with affinity for the monoamine transporters have been proposed for therapy and/or diagnosis of medical indications that include (but are not limited to) attention deficit hyperactivity disorder (ADHD), Parkinson's disease, cocaine addiction, smoking cessation, weight reduction, obsessive-compulsive disorder, various forms of depression, traumatic brain injury, stroke, and narcolepsy. Examples of monoamine transporters include, e.g., the dopamine transporter (DAT), serotonin transporter (SERT) or norepinephrine transporter (NET).

Therapies for treating diseases and disorders related to monoamine transport are needed. For example, there is a need for protective agents for neurodegenerative diseases such as Parkinson's disease and Alzheimer's disease as well as therapeutic agents for dopamine related dysfunction such as Attention Deficit Disorder. Compounds that inhibit monoamine reuptake in the mammalian system are sought to provide such therapies.

Other neuropsychiatric disorders, including Tourette's Syndrome and Lesch Nyhan Syndrome and possibly Rett's syndrome, are also marked by changes in DAT density. The DAT also is the target of the most widely used drug for attention deficit disorder, methylphenidate. The capacity to monitor the transporter in persons suffering from this disorder can have diagnostic and therapeutic implications.

The density of the DAT in the brains of substance abusers has also been shown to deviate from that in normal brain. For example, the density is elevated in post-mortem tissues of cocaine abusers (Little et al., Brain Res. 1993, 628, 17-25). On the other hand, the density of the DAT in chronic nonviolent alcohol abusers is decreased markedly. (Tiihonen et al., Nature Medicine 1995, 1, 654-657). Brain imaging of substance abusers can be useful for understanding the pathological processes of cocaine and alcohol abuse and monitoring restoration of normal brain function during treatment.

Accordingly, compounds that bind to the DAT provide important clinical information to assist in the diagnosis and treatment of these and other DAT related disease states.

Serotonin (5-hydroxytryptamine) neurotransmission is regulated and terminated by active transport via the serotonin transporter (SERT). Inhibition of 5-hydroxytryptamine reuptake has an effect on diseases mediated by 5HT receptors. Compounds that provide such inhibition can be useful, for example, as therapeutic anti-depressants. Structurally related to dopamine and norepinephrine transporters (Nelson N. 1998. J Neurochem 71:1785-1803), the SERT is the primary site of action of diverse antidepressant drugs, ranging from tricyclics such as imipramine and amitriptyline, to serotonin selective reuptake inhibitors (SSRI's) such as citalopram, fluoxetine and sertraline.

Antidepressant drugs delay the removal of extracellular serotonin from the synapse by blocking serotonin transport, thereby prolonging the duration of serotonin receptor activity. The increased availability of serotonin triggers a cascade of neuroadaptive processes, which produces symptom relief after two to four weeks. Presently known antidepressants also produce certain side effects and may selectively alleviate specific symptoms of depression (Nestler E J. 1998. Biol Psychiatry 44:526-533). Thus, it is desirable to develop novel antidepressants. The majority of clinically approved drugs to treat depression or obsessive-compulsive disorder are high affinity inhibitors of serotonin and/or norepinephrine transport. Of these transporter inhibitors, none are tropane analogs.

Norepinephrine regulates mood, is involved in learning and memory, and controls endocrine and autonomic functions. Dysfunction of norepinephrine neurotransmission has been implicated in depression, cardiovascular and thermal pathophysiology. The norepinephrine transporter (NET) regulates extracellular levels of norepinephrine in brain, in heart, and in the sympathetic nervous system. Clinically, the norepinephrine transporter is a principal target of selective or non-selective anti-depressant drugs and stimulant drugs of abuse such as cocaine and amphetamines. Blockade of the norepinephrine transporter is implicated in appetite suppression. Gehlert et al. J. Pharmacol. Exp. Ther. 287:122-127 (1998). Imaging of the norepinephrine transporter may also be useful for viewing the status of sympathetic innervation in the heart and in other adrenergic terminals, and for detecting neuroblastomas. Hadrich et al. J. Med. Chem. 42:3010-3018 (1999); Raffel et al., J. Nucl. Med. 40:323-330 (1999).

Monoamine transporters such as, the dopamine transporter, serotonin transporter and norepinephrine transporter, are localized on monoamine nerve terminals. Compounds that bind to these sites can be useful as (i) probes for neurodegenerative diseases (e.g., Parkinson's disease), (ii) therapeutic drugs for neurodegenerative diseases (e.g., Parkinson's and Alzheimer's disease), (iii) therapeutic drugs for dopamine dysfunction (e.g., Attention Deficit Disorder), (iv) treatment of psychiatric dysfunction (e.g., depression) and (v) treatment of clinical dysfunction (e.g., migraine).

It is desirable to avoid unwanted side effects of treatments targeting monoamine transporters, to the extent possible. It is also desirable to produce efficient and effective diagnostics for various conditions involving monoamine transporters.

Furthermore, it would be useful to improve the bioavailability of compounds used to treat and/or diagnose monoamine transporter related diseases and disorders. It would be useful to modify these compounds to block or reduce metabolism of the compounds, while maintaining, or ideally, improving potency and/or selectivity of the compounds.

It would also be useful to have compounds that are prodrugs, i.e., a compound that undergoes chemical conversion by an organism or enzyme preparation before exhibiting its pharmacological effects. Prodrugs are drugs containing specialized non-toxic protective groups used in a transient manner to alter or to eliminate undesirable properties in the parent molecule.

SUMMARY OF THE INVENTION

The present invention relates to tropane compounds having the following general formula:

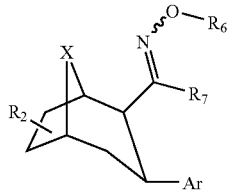

Formula I

Where:
the 2-, 3-, 6-, or 7-positions are α or β;
the compounds are racemic or 1R- or 1S-configured;
X=O, $NR_3$, $NR_{10}$, $CHR_3$, $CHR_1$, $CH_2$, $CHW_1$, $CW_1W_1$, CO, S, SO, $SO_2$, $NSO_2R_3$, $NSO_2R_{11}$ or $CX_2W$, with the N, C, O or S atom being a member of the ring;
Ar=Phenyl or 1-naphthyl or 2-naphthyl, unsubstituted or substituted with one or more group selected from: —H; —Br; —Cl; —I; —F; —OH; —$CH_3$; —$OCH_3$; —$CF_3$; —$NO_2$; —$NH_2$; —CN; —$NHCOCH_3$, —$C(CH_3)_3$, —$C(CH_2)CH_3$, $(CH_2)_qCH_3$, where q=0-6; —$COCH_3$; OAc; alkyl; alkenyl; alkynyl; allyl; isopropyl; isobutyl; wherein each substitutent can be at the 2, 3 and/or 4 position of the ring;
W or $X_2$=H, OH, $OCH_3$, OAc, $OCOR_4$, $CH_3$, $(CH_2)_nCH_3$, $R_4$;
$W_1$=H, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$;
$R_2$=$R_3$, $OR_3$, isopropyl, isobutyl, $OCOR_4$, $OCOR_5$, $W_1$, $CH_2R_3$, $OCOR_3$, $NHR_3$, $COR_3$, $(CH_2)_nCOOR_3$;
$R_3$=H, $CH_3$, $CH_2Ar$, $(CH_2)_nAr$, Ar, alkyl, alkenyl or alkynyl, cycloalkylmethyl, $CH_2CH=CHZ$, $(CH_2)_nOH$, $(CH_2)_nOR_4$, CH=CHZ; $CH_2J$-Maleimide, $CH_2JN$-Maleimide where J=$CH_2$ or O; $(CH_2)_nOCOCH_3$; $(CH_2)_nOCOCH_2OCH_3$; $(CH_2)_n$-morpholine; $(CH_2)_n$-piperidine; $(CH_2)_n$-piperazine;
$R_4$=$CH_3$, $CH_2CH_3$, alkyl, alkenyl, alkynyl, allyl, isopropyl, isobutyl;
$R_5$=H, $CH_3$, $(CH_3)_2$, $(CH_2)_nSO_3Q$, alkyl, $(alkyl)_2$, alkenyl, alkynyl, Ar, $OCH_3$;
Q=$K^+$, $Na^+$, $Li^+$, $Ca^{2+}$, $NH_4^+$, $RNH_3^+$, or other pharmaceutically acceptable salts;
$R_{10}$=$COR_4$, $CH_2OH$, $(CH_2)_nOH$, $(CH_2)_nOR_4$, $(CH_2)_nCOOR_3$, $(CH_2)_nOCOR_3$;
$R_{11}$=H, $COOCH_3$, $COOR_4$, $COR_4$, $CH_2OH$, $(CH_2)_nOH$, $(CH_2)_nOR_4$, $CR_3$=$NOR_3$, CH=$NR_3$;
$R_6$ and $R_7$ independently=H, $CH_3$, $CH_2CH_3$, $(CH_2)_rCH_3$, $(CH_2)_rAr$, isopropyl, isobutyl, CH=CH—$(CH_2)_rCH_3$, $CH_2CH=CH—(CH_2)_rCH_3$, $(CH_2)_sCH=CH—(CH_2)_rCH_3$, C≡C—$(CH_2)_rCH_3$, $CH_2C≡C—(CH_2)_rCH_3$, $(CH_2)_sC≡C—(CH_2)_rCH_3$, $OCOR_3$, $(CH_2)_dOCOR_3$, $COOR_3$ or $(CH_2)_dCOOR_3$;
d=1-6;
r=0-4;
s=0-4;
n=0-4; and
Z=F, Cl, I or Br.

The substituents at the 2 and 3 position of the ring can be α- or β-. Although the imine group is illustrated in the 2-position, it should be recognized that substitution at the 4-position is also included and the position is dependent on the numbering of the tropane ring. The compounds of the present invention can be racemic, pure R-enantiomers, or pure S-enantiomers. Thus, the structural formulas illustrated herein are intended to represent each enantiomer and diastereomer of the illustrated compound.

In certain embodiments, the compounds have one of the following formulae:

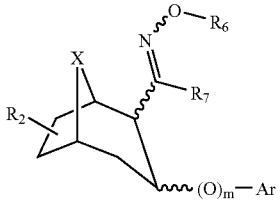

Formula III

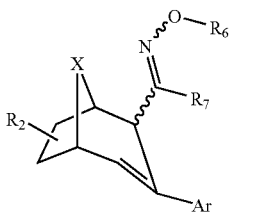

Formula IV

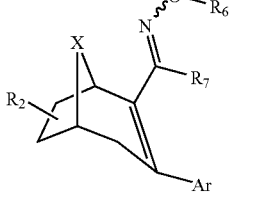

Formula V where the substituents are as described above and below and m=0-4.

The present invention also relates to tropane compounds having the following general formula:

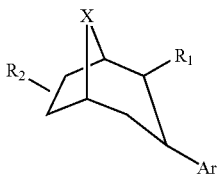

Formula VI

Where:
the 2-, 3-, 6-, or 7-positions are α or β;
the compounds are racemic or 1R- or 1S-configured;
X=O, $NR_3$, $NR_{10}$, $CHR_3$, $CHR_1$, $CH_2$, $CHW_1$, $CW_1W_1$, CO, S, SO, $SO_2$, $NSO_2R_3$, $NSO_2R_{11}$ or $CX_2W$, with the N, C, O or S atom being a member of the ring;
Ar=Phenyl or 1-naphthyl or 2-naphthyl, unsubstituted or substituted with one or more group selected from: —H; —Br; —Cl; —I; —F; —OH; —$CH_3$; —$OCH_3$; —$CF_3$; —$NO_2$; —$NH_2$; —CN; —$NHCOCH_3$, —$C(CH_3)_3$, —$C(CH_2)CH_3$, $(CH_2)_qCH_3$, where q=0-6; —$COCH_3$; OAc; alkyl; alkenyl; alkynyl; allyl; isopropyl; isobutyl; wherein each substitutent can be at the 2, 3 and/or 4 position of the ring;

W or $X_2$=H, OH, $OCH_3$, OAc, $OCOR_4$, $CH_3$, $(CH_2)_nCH_3$, $R_4$;
$W_1$=H, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$;
$R_3$=H, $CH_3$, $CH_2Ar$, $(CH_2)_nAr$, Ar, alkyl, alkenyl or alkynyl, cycloalkylmethyl, $CH_2CH=CHZ$, $(CH_2)_nOH$, $(CH_2)_nOR_4$, $CH=CHZ$; $CH_2J$-Maleimide, $CH_2JN$-Maleimide where J=$CH_2$ or O; $(CH_2)_nOCOCH_3$; $(CH_2)_nOCOCH_2OCH_3$; $(CH_2)_n$-morpholine; $(CH_2)_n$-piperidine; $(CH_2)_n$-piperazine;
$R_4$=$CH_3$, $CH_2CH_3$, alkyl, alkenyl, alkynyl, allyl, isopropyl, isobutyl;
$R_5$=H, $CH_3$, $(CH_3)_2$, $(CH_2)_nSO_3Q$, alkyl, (alkyl)$_2$, alkenyl, alkynyl, Ar, $OCH_3$;
Q=$K^+$, $Na^+$, $Li^+$, $Ca^{2+}$, $NH_4^+$, $RNH_3^+$, or other pharmaceutically acceptable salts;
$R_{10}$=$COR_4$, $CH_2OH$, $(CH_2)_nOH$, $(CH_2)_nOR_4$, $(CH_2)_nCOOR_3$, $(CH_2)_nOCOR_3$;
$R_2$=$R_3$, $OR_3$, isopropyl, isobutyl, $OCOR_4$, $OCOR_5$, $W_1$, $CH_2R_3$, $OCOR_3$, $NHR_3$, $COR_3$, $(CH_2)_nCOOR_3$;
$R_1$=H, $(CH_2)_nOH$, $(CH_2)_nOR_4$, $CR_3=NOR_3$, $CH=NR_3$; $COOR_8$, $COR_8$, $CONHR_8$, $CONR_8R_8$, $CH_2CH_3$, $(CH_2)_nCH_3$, $CHCHR_9$, $(CH_2)_nCCR_9$, $(CH_2)_nCOOR_8$, $(CH_2)_nOCOR_8$, $OCOR_8$, $C_3HNOR_9$ or $C_2N_2OR_9$;
$R_8$=$R_3$, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$; $C(CH_3)_3$, $C_{10}H_7$ or $C_{10}H_6W_1$;
$R_9$=$COOR_8$, $CH_3$, $(CH_2)_nCH_3$, $C_6H_5$, $C_6H_4Y$, $C_{10}H_7$ or $C_{10}H_6W_1$;
n=0-4; and
Z=F, Cl, I or Br;

wherein at least one of X, $R_2$ or $R_1$ comprises a $COOR_3$ group or a $OCOR_3$ group and wherein $R_3$ comprises an alkyl, cycloalkylmethyl, alkenyl or alkynyl group having from about 10 to 20 carbon atoms.

The substitutions on the Ar group of these compounds can be at any position, i.e., at the 2, 3 or 4 position, that is chemically possible based upon the selected substituent and Ar group. In certain embodiments, e.g., the substituent has the following positions: 4-F, 4-Cl, 4-I, 2-F, 2-Cl, 2-I, 3-F, 3-Cl, 3-I.

The invention also relates to pharmaceutical compositions comprising a pharmaceutically acceptable carrier and a therapeutically effective amount of a compound according to the formulas shown herein.

The invention also relates to a method for treating a patient by administering to the patient a compound of the present invention in a dose effective amount to inhibit a monoamine transporter. In another embodiment, the invention relates to a method of treating a medical condition comprising administering to a patient a compound as described herein, wherein said medical condition being attention deficit hyperactivity disorder (ADHD), Parkinson's disease, cocaine addiction, smoking cessation, weight reduction, obsessive-compulsive disorder, various forms of depression, traumatic brain injury, stroke or narcolepsy and other disorders described herein.

The invention further relates to a method of making a medicament for treating attention deficit hyperactivity disorder (ADHD), Parkinson's disease, cocaine addiction, smoking cessation, weight reduction, obsessive-compulsive disorder, various forms of depression, traumatic brain injury, stroke or narcolepsy, said method comprising formulating a compound as described herein into said medicament.

The invention also relates to a method of screening compounds for use as a treatment for altering monoamine transport, comprising exposing cells having associated monoamine transporters to a compound as described herein, and assessing binding of the compound to the cells.

The invention also relates to methods of diagnosing a disease that affects monoamine transport comprising labeling a compound as described herein, administering the labeled compound to a patient, imaging the binding of the labeled compound in the patient, and comparing said imaged patient binding to a reference standard. In certain embodiments, the reference standard is that of a normal human subject lacking a disease or disorder of the nervous system, such that the imaged patient binding can be determined to be similar or dissimilar to the binding of the normal human subject. Preferably, such method is used to diagnose a disease or disorder affecting the patient.

The details of one or more embodiments of the invention are set forth in the accompanying structures and the description below. Other features, objects, and advantages of the invention will be apparent from the following description and structures, and from the claims.

DETAILED DESCRIPTION OF FIGURES

DETAILED DESCRIPTION OF THE INVENTION

As noted above, the compounds of this invention comprise tropane compounds having an imine function at the C 2 position, having the structure:

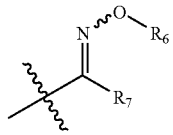

which may be synthesized from the corresponding ketone by standard techniques using an appropriate amine. When this C2 imine function is added to a tropane compound, the compound displays increased bioavailability and resistance to degradation by gastric acid (see e.g., Palani et al., *J. Med. Chem.* 44:3339, 2001). While the imine group is generally described as being at the C2, it should be recognized that substitution at the C4 position is also included and the position is dependent on the numbering of the tropane ring.

Numerous tropane-based compounds have been described and are suitable for substitution at the C2 position with the imine function of the invention. Synthesis of representative tropanes is described, for example, in U.S. Pat. Nos. 5,493,026, 5,506,359, 5,770,180, 5,853,696, 5,948,933, 6,171,576, 6,353,105 and 6,358,492, and in application Ser. Nos. 09/568,106, 09/671,534, 09/875,523, 09/932,302, 10/033,621, 10/085,482, 10/222,530, 60/327,963, which are incorporated herein in their entirety.

2β-carbomethoxy-3β-(4-fluorophenyl)-8-(3E-iodopropen-2-yl) nortropane and related compounds are described in U.S. Pat. No. 5,493,026. and include compounds having the following formula:

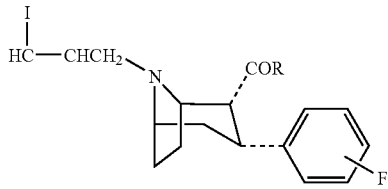

Formula II wherein:

R is —$CH_3$, —$CH_2CH_3$ (with α-COR configuration, β-COR configuration or both), $CH(CH_3)_2$, —$(CH_2)_nCH_3$, —$(CH_2)_nC_6H_4X$, —$C_6H_4X$, —$C_6H_5$, —$OCH_3$, —$OCH_3CH_2$, —$OCH(CH_3)_2$, —$OC_6H_5$, —$OC_6H_4X$, —$O(CH_2)_nC_6H_4X$, or —$(CH_2)_nCH_3$;

wherein X is —Br, —Cl, —I, —F, —OH, —$OCH_3$, —$CF_3$, —$NO_2$, —$NH_2$, —CN, —$NHCOCH_3$, —$N(CH_3)_2$, —$(CH_2)_nCH_3$, $CHOCH_3$, or —$C(CH_3)_3$ and n is between 0 and 6 inclusive.

Figure 8:
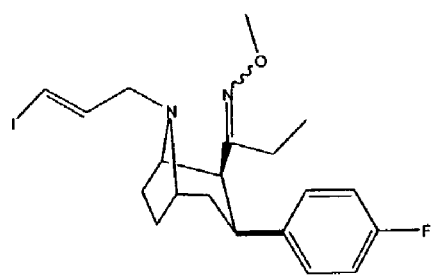
FIG. 8 shows examples of compounds of the present invention based on Formula II.
Figure 8:
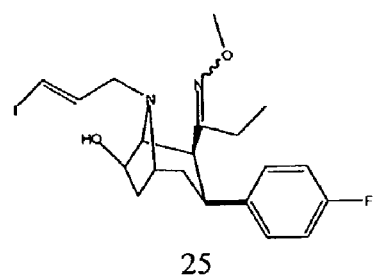
Figure 8:
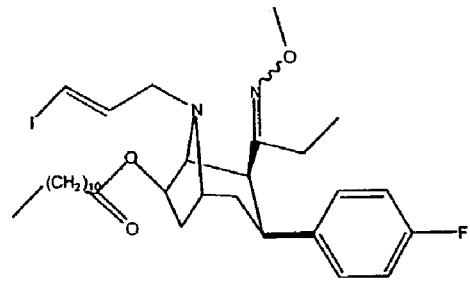
Figure 8:
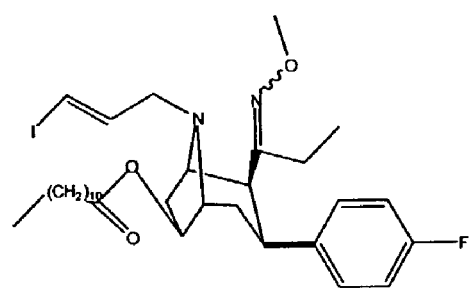

Examples of compounds, which are based on the compound shown in Formula II, are shown in FIG. 8 and include, but are a not limited to, 1-[3β-(4-Fluoro-phenyl)-8-(3-iodo-allyl)-8-aza-bicyclo[3.2.1]oct-2β-yl]-propan-1-one O-methyl-oxime (24), 1-[3β-(4-Fluoro-phenyl)-7β-hydroxy-8-(3-iodo-allyl)-8-aza-bicyclo[3.2.1]oct-2β-yl]-propan-1-one O-methyl-oxime (25), dodecanoic acid 3β-(4-fluoro-phenyl)-8-(3-iodo-allyl)-4β-(1-methoxyimino-propyl)-8-aza-bicyclo[3.2.1]oct-6β-yl ester (26) and dodecanoic acid 3β-(4-fluoro-phenyl)-8-(3-iodo-allyl)-2β-(1-methoxyimino-propyl)-8-aza-bicyclo[3.2.1]oct-6β-yl ester (27).

Other compounds can have the same formula, except that the substituent on the N-allyl group can be any halogen, preferably —I or —F. Other useful compounds may have the 2 substituent in the β position, the 3 substituent in the β position, R being —O—$CH_3$, and/or the 8 substituent being either the E isomer or the Z isomer. The halo substituent on the N-allyl moiety may be —I, —Br (particularly a radionuclide of —I or —Br) or labeled with $^{18}F$. One embodiment of the compound of the invention is 2-β-carbomethoxy-3-β-(4-fluorophenyl)-8-(3E-iodopropen-2-yl) nortropane. The compounds used in the present methods may contain a radioactive label (such as a gamma or position emitter such as $^{123}I$, $^{125}I$ $^{18}F$ or $^{11}C$ $^{123}I$,) or a $^{18}F$ fluoro label as part of the 3-halopropen-2-yl substituent.

In one embodiment of the present invention, tropane analogs are provided having substituents in the 6- or 7-position of the tropane structure, including those having one of the following formulae:

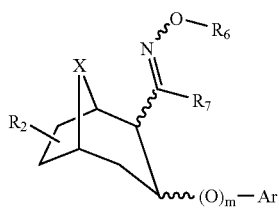

Formula III

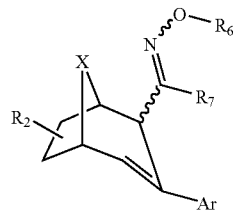

Formula IV

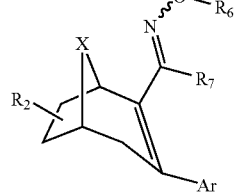

Formula V

Where:

the 2-, 3-, 6-, or 7-positions are α or β;

the compounds are racemic or 1R- or 1S-configured;

X=O, $NR_3$, $NR_{10}$, $CHR_3$, $CHR_1$, $CH_2$, $CHW_1$, $CW_1W_1$, CO, S, SO, $SO_2$, $NSO_2R_3$, $NSO_2R_{11}$ or $CX_2W$, with the N, C, O or S atom being a member of the ring;

Ar=Phenyl or 1-naphthyl or 2-naphthyl, unsubstituted or substituted with one or more group selected from: —H; —Br; —Cl; —I; —F; —OH; —$CH_3$; —$OCH_3$; —$CF_3$; —$NO_2$; —$NH_2$; —CN; —$NHCOCH_3$, —$C(CH_3)_3$, —$C(CH_2)$ $CH_3$, $(CH_2)_qCH_3$, where q=0-6; —$COCH_3$; OAc; alkyl; alkenyl; alkynyl; allyl; isopropyl; isobutyl; wherein each substitutent can be at the 2, 3 and/or 4 position of the ring;

W or $X_2$=H, OH, $OCH_3$, OAc, $OCOR_4$, $CH_3$, $(CH_2)_nCH_3$, $R_4$;

$W_1$=H, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$;

$R_2$=$R_3$, $OR_3$, isopropyl, isobutyl, $OCOR_4$, $OCOR_5$, $W_1$, $CH_2R_3$, $OCOR_3$, $NHR_3$, $COR_3$, $(CH_2)_nCOOR_3$;

$R_3$=H, $CH_3$, $CH_2Ar$, $(CH_2)_nAr$, Ar, alkyl, alkenyl or alkynyl, cycloalkylmethyl, $CH_2CH=CHZ$, $(CH_2)_nOH$, $(CH_2)_nOR_4$, CH=CHZ; $CH_2$J-Maleimide, $CH_2$JN-Maleimide where J=$CH_2$ or O; $(CH_2)_nOCOCH_3$; $(CH_2)_nOCOCH_2OCH_3$; $(CH_2)_n$-morpholine; $(CH_2)_n$-piperidine; $(CH_2)_n$-piperazine;

$R_4$=$CH_3$, $CH_2CH_3$, alkyl, alkenyl, alkynyl, allyl, isopropyl, isobutyl;

$R_5$=H, $CH_3$, $(CH_3)_2$, $(CH_2)_nSO_3Q$, alkyl, $(alkyl)_2$, alkenyl, alkynyl, Ar, $OCH_3$;

Q=$K^+$, $Na^+$, $Li^+$, $Ca^{2+}$, $NH_4^+$, $RNH_3^+$, or other pharmaceutically acceptable salts;

$R_{10}$=$COR_4$, $CH_2OH$, $(CH_2)_nOH$, $(CH_2)_nOR_4$, $(CH_2)_nCOOR_3$, $(CH_2)_nOCOR_3$;

$R_{11}$=H, $COOCH_3$, $COOR_4$, $COR_4$, $CH_2OH$, $(CH_2)_nOH$, $(CH_2)_nOR_4$, $CR_3$=$NOR_3$, CH=$NR_3$;

$R_6$ and $R_7$ independently=H, $CH_3$, $CH_2CH_3$, $(CH_2)_rCH_3$, $(CH_2)_rAr$, isopropyl, isobutyl, CH=CH—$(CH_2)_rCH_3$, $CH_2CH=CH—(CH_2)_rCH_3$, $(CH_2)_sCH=CH—(CH_2)_rCH_3$, $C\equiv C—(CH_2)_rCH_3$, $CH_2C\equiv C—(CH_2)_rCH_3$, $(CH_2)_sC\equiv C—(CH_2)_rCH_3$, $OCOR_3$, $(CH_2)_dOCOR_3$, $COOR_3$ or $(CH_2)_dCOOR_3$;

d=1-6;

r=0-4;

s=0-4;

m=0-4;

n=0-4; and

Z=F, Cl, I or Br.

In one embodiment, each of the 6- and 7-positions includes an $R_2$ as listed above.

Tropane analogs that have a 3α-aryl group generally assume a boat configuration, and those having a 3β-aryl generally have a chair configuration. Depending on the application, one configuration or the other may confer advantageous properties, such as desired selectivity or binding kinetics.

The present invention also relates to tropane compounds having the following general formula:

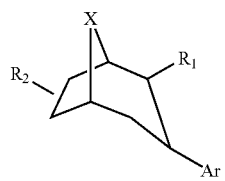

Formula VI

Where:
the 2-, 3-, 6-, or 7-positions are α or β;
the compounds are racemic or 1R- or 1S-configured;
$X=O$, $NR_3$, $NR_{10}$, $CHR_3$, $CHR_1$, $CH_2$, $CHW_1$, $CW_1W_1$, $CO$, $S$, $SO$, $SO_2$, $NSO_2R_3$, $NSO_2R_{11}$ or $CX_2W$, with the N, C, O or S atom being a member of the ring;
Ar=Phenyl or 1-naphthyl or 2-naphthyl, unsubstituted or substituted with one or more group selected from: —H; —Br; —Cl; —I; —F; —OH; —$CH_3$; —$OCH_3$; —$CF_3$; —$NO_2$; —$NH_2$; —CN; —$NHCOCH_3$, —$C(CH_3)_3$, —$C(CH_2)$ $CH_3$, $(CH_2)_qCH_3$, where q=0-6; —$COCH_3$; OAc; alkyl; alkenyl; alkynyl; allyl; isopropyl; isobutyl; wherein each substitutent can be at the 2, 3 and/or 4 position of the ring;
W or $X_2$=H, OH, $OCH_3$, OAc, $OCOR_4$, $CH_3$, $(CH_2)_nCH_3$, $R_4$;
$W_1$=H, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$;
$R_3$=H, $CH_3$, $CH_2Ar$, $(CH_2)_nAr$, Ar, alkyl, alkenyl or alkynyl, cycloalkylmethyl, $CH_2CH=CHZ$, $(CH_2)_nOH$, $(CH_2)_n OR_4$, $CH=CHZ$; $CH_2J$-Maleimide, $CH_2JN$-Maleimide where $J=CH_2$ or O; $(CH_2)_nOCOCH_3$; $(CH_2)_n OCOCH_2OCH_3$; $(CH_2)_n$-morpholine; $(CH_2)_n$-piperidine; $(CH_2)_n$-piperazine;
$R_4$=$CH_3$, $CH_2CH_3$, alkyl, alkenyl, alkynyl, allyl, isopropyl, isobutyl;
$R_5$=H, $CH_3$, $(CH_3)_2$, $(CH_2)_nSO_3Q$, alkyl, $(alkyl)_2$, alkenyl, alkynyl, Ar, $OCH_3$;
Q=$K^+$, $Na^+$, $Li^+$, $Ca^{2+}$, $NH_4^+$, $RNH_3^+$, or other pharmaceutically acceptable salts;
$R_{10}$=$COR_4$, $CH_2OH$, $(CH_2)_nOH$, $(CH_2)_nOR_4$, $(CH_2)_n COOR_3$, $(CH_2)_nOCOR_3$;
$R_2$=$R_3$, $OR_3$, isopropyl, isobutyl, $OCOR_4$, $OCOR_5$, $W_1$, $CH_2R_3$, $OCOR_3$, $NHR_3$, $COR_3$, $(CH_2)_nCOOR_3$;
$R_1$=H, $(CH_2)_nOH$, $(CH_2)_nOR_4$, $CR_3=NOR_3$, $CH=NR_3$; $COOR_8$, $COR_8$, $CONHR_8$, $CONR_8R_8$, $CH_2CH_3$, $(CH_2)_n CH_3$, $CHCHR_9$, $(CH_2)_nCCR_9$, $(CH_2)_nCOOR_8$, $(CH_2)_nO$-$COR_8$, $OCOR_8$, $C_3HNOR_9$ or $C_2N_2OR_9$;
$R_8$=$R_3$, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$; $C(CH_3)_3$, $C_{10}H_7$ or $C_{10}H_6W_1$;
$R_9$=$COOR_8$, $CH_3$, $(CH_2)_nCH_3$, $C_6H_5$, $C_6H_4Y$, $C_{10}H_7$ or $C_{10}H_6W_1$;
n=0-4;
m=0-4; and
Z=F, Cl, I or Br;

wherein at least one of X, $R_2$ or $R_1$ comprises a $COOR_3$ group or a $OCOR_3$ group and wherein $R_3$ comprises an alkyl, cycloalkylmethyl, alkenyl or alkynyl group having from about 10 to 20 carbon atoms.

In compounds of Formula VI, the substituents at the 2 and 3 position of the tropane ring can be α- or β-. Although the $R_1$ group is illustrated in the 2-position, it should be recognized that substitution at the 4-position is also included and the position is dependent on the numbering of the tropane ring.

When the compounds of Formula VI are administered to a subject, they can be cleaved by an esterase at the ester linkage of the $COOR_3$ group or $OCOR_3$ group to become a more active compound. Such compounds enable the slow release of the desired compound.

Similarly, when the compounds of Formulas I, II-V have a $COOR_3$ group or $OCOR_3$ group positioned at any of $R_2$, $R_6$, $R_7$ or X positions, and the $R_3$ comprises an alkyl, cycloalkylmethyl, alkenyl or alkynyl group having from 10 to 20 carbon atoms, the esters can be cleaved by an esterase after administration to a subject to yield a more active compound.

In another embodiment of the present invention, X=N-L-Ch, where "L" is a linking moiety comprising a chain of atoms containing 2 to about 6 carbon atoms in the backbone of the chain or, if a ring is part of the chain, 1 to about 4 carbon atoms in the backbone of the chain in addition to the ring carbons; and "Ch" is a tridentate or tetradentate chelating ligand that forms a neutral complex with technetium or rhenium. The chelating ligand is covalently attached to the linker L. Preferred chelating ligands contain a plurality of N or S atoms for complexing with the radionuclide. Examples of suitable ligands are the $N_2S_2$ compounds described in U.S. Pat. No. 6,171,576. Preferred chelating ligands are those formed from monoaminomonoamide compounds having structures of formula V, VI or VII, described in U.S. Pat. No. 6,171,576, e.g., N-{2-((2-((triphenylmethyl)thio)ethyl) amino)acetyl}-S-(triphenylmethyl)-2-aminoethanethiol ("MAMA"'). Any organic linker having a backbone chain length of 2 to about 6 carbon atoms can be used to attach the chelating ligand. Examples of linkers include $(CH_2)_m$, $CH_2$ $(CH_2)_mCH_2$, $(CH_2)_mC_6H_4(CH_2)_p$, $CH_2(CHCH)CH_2$, $CH_2CCCH_2$, $(CH_2)_mNHR(CH_2)$, $(CH_2)_mO(CH_2)$, $(CH_2)_mS$ $(CH_2)$, $CH_2CONH(CH_2)_m$, $(CH_2)_mCONH(CH_2)_p$, and $(CH_2)_mCOO(CH_2)_p$, where m=0-5, p=0-5, and (m+p)=1-5. These linkers are further described in U.S. Pat. No. 6,171, 576.

When these compounds are complexed with $^{99m}$technetium or rhenium they are useful as imaging agents for detecting neurodegenerative and neuropsychiatric disorders characterized by a change in density of DAT or dopamine neurons. For example, a method for detecting the change in DAT resulting from a neurodegenerative disease, such as Parkinson's disease, comprises injecting a labeled compound of the present invention in a dose effective amount for detecting DAT in the particular mammal and obtaining images of the labeled compound bound to DAT. Rhenium labeled compounds can also be useful for therapeutic treatments.

Alkyl designates aliphatic saturated branched or straight chain hydrocarbon monovalent substituents, having up to 20 carbons, including all lengths from 1 to 20. Lower alkyl designates aliphatic saturated branched or straight chain hydrocarbon monovalent substituents having 1 to about 8 carbons atoms, such as methyl, ethyl, isopropyl, n-propyl, n-butyl, $(CH_2)_nCH_3$, and $C(CH_3)_3$. Alkyl refers to both cyclic and noncyclic groups, although cyclic groups will comprise at least three carbon ring atoms.

Alkenyl and alkynyl groups of compounds of the invention have up to 20 carbons and have one or more unsaturated linkages. Also, the terms alkenyl and alkynyl as used herein refer to both cyclic and noncyclic groups.

Alkoxy groups of compounds of the invention have a length of up to 20 carbons and have one or more oxygen linkages. Lower alkoxy designates lower alkoxy substituents such as methoxy, ethoxy, or isopropoxy moieties. The lower alkyl and lower alkoxy substituents are from one to about 8 carbons in length, and in one embodiment are from one to about four carbons in length. Lower alkenyl means aliphatic unsaturated branched or straight chain vinyl hydrocarbon substituents such as allyl, etc. Lower alkynyl includes alkynyl substituents such as propyne or butyne; either of these substituent types may contain from 2 to about 8 carbon atoms, and in one embodiment from 2 to 4 carbon atoms.

Substituted alkyl, substituted alkoxy, substituted alkenyl and substituted alkynyl are intended to include corresponding alkyl, alkoxy, alkenyl or alkynyl groups substituted with halide, hydroxy, carboxylic acid, or carboxamide groups such as —CH$_2$OH, —CH$_2$CH$_2$COOH, —CH$_2$CONH$_2$, —OCH$_2$CH$_2$OH, —OCH$_2$COOH, and —OCH$_2$CH$_2$CONH$_2$.

Figure 7:
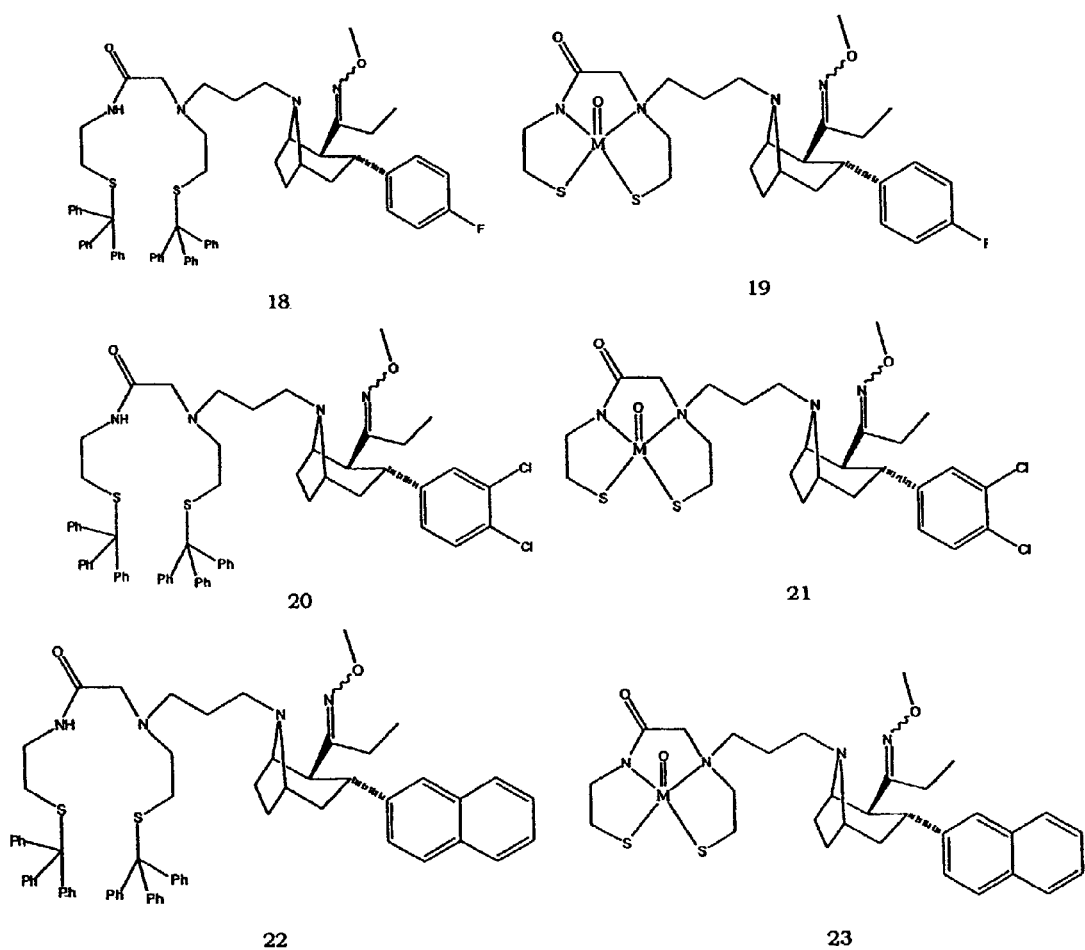
FIG. 7 shows examples of compounds of the present invention for radiolabeling.

An example of a compound containing a chelator, linker and an imine group on the C2 is shown, e.g., as compound 18, in FIG. 7. An example of such compounds, in the boat conformation includes, but is not limited to 2-[{3-[3α-(4-Fluoro-phenyl)-2β-(1-methoxyimino-propyl)-8-aza-bicyclo[3.2.1]oct-8-yl]-propyl}-(2-tritylsulfanyl-ethyl)-amino]-N-(2-tritylsulfanyl-ethyl)-acetamide. When this compound is complexed with rhenium or $^{99m}$technetium ("M"), the resulting compound has the structure shown as compound 19, in FIG. 7, (RS)-N-{2((3'N'-propyl-(1"R-3α-(4-fluorophenyl)tropane-2"β-(1-methoxyimino-propyl))(2-mercaptoethyl)amino)-acetyl)-2-aminoethanethiolato}rhenium(V) oxide and (RS)-N-{2((3'N'-propyl-(1"R-3α-(4-fluorophenyl)tropane-2"β-(1-methoxyimino-propyl))(2-mercaptoethyl)amino)-acetyl)-2-aminoethanethiolato}$^{99m}$technetium(V) oxide, respectively. Another example is shown as compound 20, 2-[{3-[3α-(3,4-Dichloro-phenyl)-2β-(1-methoxyimino-propyl)-8-aza-bicyclo[3.2.1]oct-8-yl]-propyl}-(2-tritylsulfanyl-ethyl)-amino]-N-(2-tritylsulfanyl-ethyl)-acetamide. When this compound is complexed with rhenium or $^{99m}$technetium, the resulting compound has the structure shown as compound 21, in FIG. 7, (RS)-N-{2((3'N'-propyl-(1"R-3α-(3,4-dichlorophenyl)tropane-2"β-(1-methoxyimino-propyl))(2-mercaptoethyl)amino)-acetyl)-2-aminoethanethiolato}rhenium(V) oxide and (RS)-N-{2((3'N'-propyl-(1"R-3α-(3,4-dichlorophenyl)tropane-2"β-(1-methoxyimino-propyl))(2-mercaptoethyl)amino)-acetyl)-2-aminoethanethiolato}$^{99m}$technetium(V) oxide, respectively. Another example is shown as compound 22, 2-[{3-[2β-(1-Methoxyimino-propyl)-3α-naphthalen-2-yl-8-aza-bicyclo[3.2.1]oct-8-yl]-propyl}-(2-tritylsulfanyl-ethyl)-amino]-N-(2-tritylsulfanyl-ethyl)-acetamide. When this compound is complexed with rhenium or $^{99m}$technetium, the resulting compound has the structure shown as compound 23, in FIG. 7, (RS)-N-{2((3'N'-propyl-(1"R-3α-(2-naphthyl)tropane-2"β-(1-methoxyimino-propyl))(2-mercaptoethyl)amino)-acetyl)-2-aminoethanethiolato}rhenium(V) oxide and (RS)-N-{2((3'N'-propyl-(1"R-3α-(2-naphthyl)tropane-2"β-(1-methoxyimino-propyl))(2-mercaptoethyl)amino)-acetyl)-2-aminoethanethiolato}$^{99m}$technetium(V) oxide, respectively.

The names of the corresponding chair (3β-) compounds are: 2-[{3-[3β-(4-Fluoro-phenyl)-2β-(1-methoxyimino-propyl)-8-aza-bicyclo[3.2.1]oct-8-yl]-propyl}-(2-tritylsulfanyl-ethyl)-amino]-N-(2-tritylsulfanyl-ethyl)-acetamide, (RS)-N-{2((3'N'-propyl-(1"R-3β-(4-fluorophenyl)tropane-2"β-(1-methoxyimino-propyl))(2-mercaptoethyl) amino)-acetyl)-2-aminoethanethiolato}rhenium(V) oxide, (RS)-N-{2((3'N'-propyl-(1"R-3β-(4-fluorophenyl)tropane-2"β-(1-methoxyimino-propyl))(2-mercaptoethyl)amino)-acetyl)-2-aminoethanethiolato}$^{99m}$technetium(V) oxide, 2-[{3-[3β-(3,4-Dichloro-phenyl)-2β-(1-methoxyimino-propyl)-8-aza-bicyclo[3.2.1]oct-8-yl]-propyl}-(2-tritylsulfanyl-ethyl)-amino]-N-(2-tritylsulfanyl-ethyl)-acetamide, (RS)-N-{2((3'N'-propyl-(1"R-3β-(3,4-dichlorophenyl)tropane-2"β-(1-methoxyimino-propyl))(2-mercaptoethyl)amino)-acetyl)-2-aminoethanethiolato}rhenium(V) oxide, (RS)-N-{2((3'N'-propyl-(1"R-3β-(3,4-dichlorophenyl)tropane-2"β-(1-methoxyimino-propyl))(2-mercaptoethyl)amino)-acetyl)-2-aminoethanethiolato}$^{99m}$technetium(V) oxide, 2-[{3-[3β-(1-Methoxyimino-propyl)-3β-naphthalen-2-yl-8-aza-bicyclo[3.2.1]oct-8-yl]-propyl}-(2-tritylsulfanyl-ethyl)-amino]-N-(2-tritylsulfanyl-ethyl)-acetamide, (RS)-N-{2((3'N'-propyl-(1"R-3β-(2-naphthyl)tropane-2"β-(1-methoxyimino-propyl))(2-mercaptoethyl)amino)-acetyl)-2-aminoethanethiolato}rhenium(V) oxide and (RS)-N-{2((3'N'-propyl-(1"R-3β-(2-naphthyl)tropane-2"β-(1-methoxyimino-propyl))(2-mercaptoethyl)amino)-acetyl)-2-aminoethanethiolato}$^{99m}$technetium(V) oxide.

The compounds are diastereomers, the tropane can be 1R and/or 1S and the metal chelate may be R and/or S.

Figure 6:
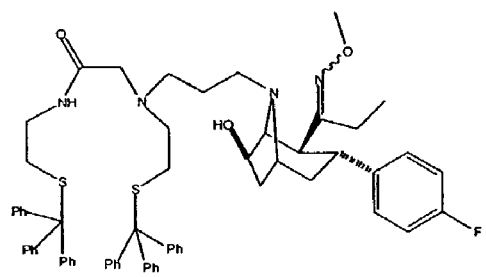
FIG. 6 shows examples of prodrugs of the present invention.
Figure 6:
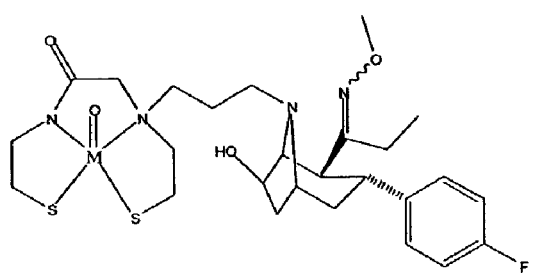
Figure 6:
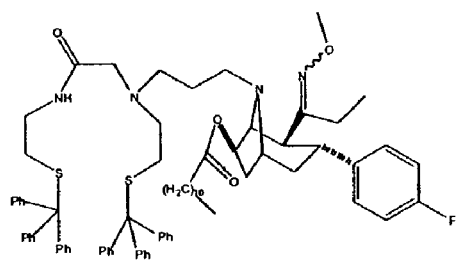
Figure 6:
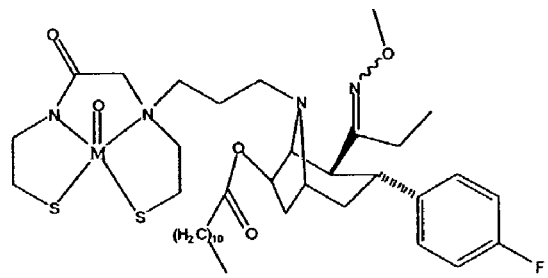

An example of a compound containing a chelator, linker, an imine group on the C2 and a OH at the 6 position, is shown, e.g., compound 14, in FIG. 6. Examples of such compounds, in the boat conformation include, but are not limited to 2-[{3-[3α-(4-Fluoro-phenyl)-7β-hydroxy-2β-(1-methoxyimino-propyl)-8-aza-bicyclo[3.2.1]oct-8-yl]-propyl}-(2-tritylsulfanyl-ethyl)-amino]-N-(2-tritylsulfanyl-ethyl)-acetamide; 2-[{3-[3α-(3,4-dichloro-phenyl)-7β-hydroxy-2β-(1-methoxyimino-propyl)-8-aza-bicyclo[3.2.1]oct-8-yl]-propyl}-(2-tritylsulfanyl-ethyl)-amino]-N-(2-tritylsulfanyl-ethyl)-acetamide and 2-[{3-[3α-(2-naphthyl)-7β-hydroxy-2β-(1-methoxyimino-propyl)-8-aza-bicyclo[3.2.1]oct-8-yl]-propyl}-(2-tritylsulfanyl-ethyl)-amino]-N-(2-tritylsulfanyl-ethyl)-acetamide. Examples in the chair conformation include, but are not limited to, 2-[{3-[3β-(4-Fluoro-phenyl)-7β-hydroxy-2β-(1-methoxyimino-propyl)-8-aza-bicyclo[3.2.1]oct-8-yl]-propyl}-(2-tritylsulfanyl-ethyl)-amino]-N-(2-tritylsulfanyl-ethyl)-acetamide, 2-[{3-[3β-(3,4-Dichloro-phenyl)-7β-hydroxy-2β-(1-methoxyimino-propyl)-8-aza-bicyclo[3.2.1]oct-8-yl]-propyl}-(2-tritylsulfanyl-ethyl)-amino]-N-(2-tritylsulfanyl-ethyl)-acetamide and 2-[{3-[3β-(2-Naphthyl)-7β-hydroxy-2β-(1-methoxyimino-propyl)-8-aza-bicyclo[3.2.1]oct-8-yl]-propyl}-(2-tritylsulfanyl-ethyl)-amino]-N-(2-tritylsulfanyl-ethyl)-acetamide.

When these compounds are complexed with rhenium or $^{99m}$technetium, the resulting compounds have the structure shown as compound 15, in FIG. 6 and include: (RS)-N-{2((3'N'-propyl-(1"R-3α-(4-fluorophenyl)-7β-hydroxy-tropane-2"β-(1-methoxyimino-propyl))(2-mercaptoethyl)amino)-acetyl)-2-aminoethanethiolato} rhenium(V) oxide, (RS)-N-{2((3'N'-propyl-(1"R-3α-(4-fluorophenyl)-7β-hydroxy-tropane-2"β-(1-methoxyimino-propyl))(2-mercaptoethyl)amino)-acetyl)-2-aminoethanethiolato}$^{99m}$technetium(V) oxide, (RS)-N-{2((3'N'-propyl-(1"R-3α-(3,4-dichlorophenyl)-7β-hydroxy-tropane-2"β-(1-methoxyimino-propyl))(2-mercaptoethyl)amino)-acetyl)-2-aminoethanethiolato}rhenium(V) oxide, (RS)-N-{2((3'N'-propyl-(1"R-3α-(3,4-dichlorophenyl)-7β-hydroxy-tropane-2"β-(1-methoxyimino-propyl))(2-mercaptoethyl)amino)-acetyl)-2-aminoethanethiolato}$^{99m}$technetium(V) oxide, (RS)-N-{2((3'N'-propyl-(1"R-3α-(2-naphthyl)-7β-hydroxy-tropane-2"β-(1-methoxyimino-propyl))(2-mercaptoethyl)amino)-acetyl)-2-aminoethanethiolato}rhenium(V) oxide, and (RS)-N-{2((3'N'-propyl-(1"R-3α-(2-naphthyl)-7β-hydroxy-tropane-2"β-(1-methoxyimino-propyl))(2-mercaptoethyl)amino)-acetyl)-2-aminoethanethiolato}$^{99m}$technetium(V) oxide.

The corresponding compounds that have the chair conformation are 3β compounds and include: (RS)-N-{2((3'N'-propyl-(1"R-3β-(4-fluorophenyl)-7β-hydroxy-tropane-2"β-(1-methoxyimino-propyl))(2-mercaptoethyl)amino)-acetyl)-2-aminoethanethiolato}rhenium(V) oxide, (RS)-N-{2((3'N'-propyl-(1"R-3β-(4-fluorophenyl)-7β-hydroxy-tropane-2"β-(1-methoxyimino-propyl))(2-mercaptoethyl)amino)-acetyl)-2-aminoethanethiolato} $^{99m}$technetium(V) oxide, (RS)-N-{2((3'N'-propyl-(1"R-3β-(3,4-dichlorophenyl)-7β-hydroxy-tropane-2"β-(1-methoxyimino-propyl))(2-mercaptoethyl)amino)-acetyl)-2-aminoethanethiolato}rhenium(V) oxide, (RS)-N-{2((3'N'-propyl-(1"R-3β-(3,4-dichlorophenyl)-7β-hydroxy-tropane-2"β-(1-methoxyimino-propyl))(2-mercaptoethyl)amino)-acetyl)-2-aminoethanethiolato}$^{99m}$technetium(V) oxide, (RS)-N-{2((3'N'-propyl-(1"R-3β-(2-naphthyl)-7β-hydroxy-tropane-2"β-(1-methoxyimino-propyl))(2-mercaptoethyl)amino)-acetyl)-2-aminoethanethiolato}rhenium(V) oxide, and (RS)-N-{2((3'N'-propyl-(1"R-3β-(2-naphthyl)-7β-hydroxy-tropane-2"β-(1-methoxyimino-propyl))(2-mercaptoethyl)amino)-acetyl)-2-aminoethanethiolato}$^{99m}$technetium(V) oxide.

An example of a compound containing a chelator, linker, an imine group on the C2 and which is a prodrug is shown, e.g., as compound 16, in FIG. 6. Examples of such compounds, in the boat conformation include, but are not limited to dodecanoic acid 3α-(4-fluoro-phenyl)-4β-(1-methoxyimino-propyl)-8-(3-{(2-tritylsulfanyl-ethyl)-[(2-tritylsulfanyl-ethylcarbamoyl)-methyl]-amino}-propyl)-8-aza-bicyclo[3.2.1]oct-6β-yl ester, dodecanoic acid 3α-(3,4-dichloro-phenyl)-4β-(1-methoxyimino-propyl)-8-(3-{(2-tritylsulfanyl-ethyl)-[(2-tritylsulfanyl-ethylcarbamoyl)-methyl]-amino}-propyl)-8-aza-bicyclo[3.2.1]oct-6β-yl ester and dodecanoic acid 3α-(2-naphthyl)-4β-(1-methoxyimino-propyl)-8-(3-{(2-tritylsulfanyl-ethyl)-[(2-tritylsulfanyl-ethylcarbamoyl)-methyl]-amino}-propyl)-8-aza-bicyclo[3.2.1] oct-6β-yl ester. Examples in the chair conformation include, but are not limited to, dodecanoic acid 3β-(4-fluoro-phenyl)-4β-(1-methoxyimino-propyl)-8-(3-{(2-tritylsulfanyl-ethyl)-[(2-tritylsulfanyl-ethylcarbamoyl)-methyl]-amino}-propyl)-8-aza-bicyclo[3.2.1]oct-6β-yl ester, dodecanoic acid 3β-(3,4-dichloro-phenyl)-4β-(1-methoxyimino-propyl)-8-(3-{(2-tritylsulfanyl-ethyl)-[(2-tritylsulfanyl-ethylcarbamoyl)-methyl]-amino}-propyl)-8-aza-bicyclo[3.2.1]oct-6β-yl ester and dodecanoic acid 3β-(2-naphthyl)-4β-(1-methoxyimino-propyl)-8-(3-{(2-tritylsulfanyl-ethyl)-[(2-tritylsulfanyl-ethylcarbamoyl)-methyl]-amino}-propyl)-8-aza-bicyclo[3.2.1] oct-6β-yl ester.

When these compounds are complexed with rhenium or $^{99m}$technetium ("M"), the resulting compounds have the structure shown as compound 17, in FIG. 6 and include: (RS)-N-{2((3'N'-propyl-(1"R-3α-(4-fluorophenyl)-7β-dodecanoyloxy-tropane-2"β-(1-methoxyimino-propyl))(2-mercaptoethyl)amino)-acetyl)-2-aminoethanethiolato}rhenium(V) oxide, (RS)-N-{2((3'N'-propyl-(1"R-3α-(4-fluorophenyl)-7β-dodecanoyloxy-tropane-2"β-(1-methoxyimino-propyl))(2-mercaptoethyl)amino)-acetyl)-2-aminoethanethiolato} $^{99m}$technetium(V) oxide; (RS)-N-{2((3'N'-propyl-(1"R-3α-(3,4-dichlorophenyl)-7β-dodecanoyloxy-tropane-2"β-(1-methoxyimino-propyl))(2-mercaptoethyl)amino)-acetyl)-2-aminoethanethiolato} rhenium(V) oxide, (RS)-N-{2((3'N'-propyl-(1"R-3α-(3,4-dichlorophenyl)-7β-dodecanoyloxy-tropane-2"β-(1-methoxyimino-propyl))(2-mercaptoethyl)amino)-acetyl)-2-aminoethanethiolato}$^{99m}$technetium(V) oxide, (RS)-N-{2 ((3'N'-propyl-(1"R-3α-(2-naphthyl)-7β-dodecanoyloxy-tropane-2"β-(1-methoxyimino-propyl))(2-mercaptoethyl) amino)-acetyl)-2-aminoethanethiolato}rhenium(V) oxide, and (RS)-N-{2((3'N'-propyl-(1"R-3α-(2-naphthyl)-7β-dodecanoyloxy-tropane-2"β-(1-methoxyimino-propyl))(2-mercaptoethyl)amino)-acetyl)-2-aminoethanethiolato}$^{99m}$technetium(V) oxide.

Examples of chair compounds include: (RS)-N-{2((3'N'-propyl-(1"R-3β-(4-fluorophenyl)-7β-dodecanoyloxy-tropane-2"β-(1-methoxyimino-propyl))(2-mercaptoethyl) amino)-acetyl)-2-aminoethanethiolato} rhenium(V) oxide, (RS)-N-{2((3'N'-propyl-(1"R-3β-(4-fluorophenyl)-7β-dodecanoyloxy-tropane-2"β-(1-methoxyimino-propyl))(2-mercaptoethyl)amino)-acetyl)-2-aminoethanethiolato} $^{99m}$technetium(V) oxide, (RS)-N-{2((3'N'-propyl-(1"R-3β-(3,4-dichlorophenyl)-7β-dodecanoyloxy-tropane-2"β-(1-methoxyimino-propyl))(2-mercaptoethyl)amino)-acetyl)-2-aminoethanethiolato}rhenium(V) oxide, (RS)-N-{2((3'N'-propyl-(1"R-3β-(3,4-dichlorophenyl)-7β-dodecanoyloxy-tropane-2"β-(1-methoxyimino-propyl))(2-mercaptoethyl) amino)-acetyl)-2-aminoethanethiolato}$^{99m}$technetium(V) oxide, (RS)-N-{2((3'N'-propyl-(1"R-3β-(2-naphthyl)-7β-dodecanoyloxy-tropane-2"β-(1-methoxyimino-propyl))(2-mercaptoethyl)amino)-acetyl)-2-aminoethanethiolato} rhenium(V) oxide, and (RS)-N-{2((3'N'-propyl-(1"R-3β-(2-naphthyl)-7β-dodecanoyloxy-tropane-2"β-(1-methoxyimino-propyl))(2-mercaptoethyl)amino)-acetyl)-2-aminoethanethiolato} $^{99m}$technetium(V) oxide.

The compounds of the present invention can be selected on the basis of their selectivity of binding to one type of monoamine transporter as compared with another type. For example, certain compounds of the invention preferentially bind to SERT rather than DAT, and one such compound might be selected for use in a diagnostic procedure that evaluated a condition characterized by a change in density, distribution or number of SERT without a corresponding change in DAT.

Monoamine reuptake by a monoamine transporter can be inhibited by contacting the monoamine transporter with a reuptake-inhibiting amount of a compound of the present invention. A reuptake-inhibiting amount of a compound of the invention may be administered to a mammal in a pharmaceutically acceptable carrier.

Medical indications which may be diagnosed or treated with the compounds of the invention include attention deficit hyperactivity disorder (ADHD); Parkinson's disease; cocaine addiction; smoking cessation; weight reduction; obsessive-compulsive disorder; various forms of depression; traumatic brain injury; stroke; narcolepsy; seasonal affective disorders; sexual dysfunction; sexual behavior disorders; learning deficit; disorders involving the release of acetylcholine, including memory deficits, senile dementia, dementia of aging, AIDS-dementia, pseudodementia, presenile dementia, autism, mutism, cognitive disorders, dyslexia, tardive dyskinesia, hyperkinesias, anxiety, panic disorders, paranoia, post-traumatic syndrome; social phobia, other phobias; psychosis; bipolar disorder and other psychiatric or clinical dysfunctions; mania; manic depression; schizophrenia (deficient form and productive form); acute or chronic extrapyramidal symptoms induced by neuroleptic agents; chronic fatigue syndrome; deficits of alertness, attention, arousal and vigilance; disorders of sleep and jet-lag; obesity, bulimia, anorexia nervosa and other eating disorders; cocaine and other drug addiction or misuse; alcoholism; neurological disorders; epilepsy; neurodegenerative diseases including Alzheimer Disease, Huntington Disease, Amyotrophic Lateral Sclerosis, Gilles de la Tourette syndrome; mild, moderate or severe pain of acute, chronic or recurrent character, pain caused by migraine, postoperative pain, or phantom limb pain; disorders linked to decreased transmission of serotonin in mammals, including Ganser syndrome, migraine headache, premenstrual syndrome or late luteal phase syndrome, or peripheral neuropathy.

The invention also includes methods of making medicaments for treating the above indications, as well as pharmaceutical compositions containing the compounds with pharmaceutically acceptable carrier or other formulation components.

The invention also includes the use of the above compounds diagnostically or in research to determine physiological conditions associated with altered function, distribution, number or density of dopamine, norepinephrine or serotonin transporters, such as may be associated with behavioral and neurodegenerative disorders or diseases. A labeled compound of the invention can be useful to compare the current status of a medical condition with that at another time, or to evaluate the effect of a therapeutic procedure or treatment. For imaging purposes, the compounds may be labeled by substituting an atom of the compound with a corresponding radioisotope. For example, H may be substituted with $^3$H, or F with $^{18}$F. Alternatively, a radioactive substituent may be added to the compound. Or, as described above, rhenium or $^{99m}$technetium may be used to form a chelated complex for imaging.

For example, a method for detecting the change in DAT resulting from a neurodegenerative disease, such as Parkinson's disease, comprises injecting a labeled compound of the present invention in a dose effective amount for detecting DAT in the particular mammal and obtaining images of the labeled compound bound to DAT.

As aforesaid, dysfunction of monoamine transporters has been implicated in several neuropsychiatric diseases and other types of disorders as indicated above. Imaging of the transporters offers important clinical information relevant to diagnosis and therapeutic treatments. Compounds that bind to monoamine transporters of interest can be labeled for use as imaging agents for PET or for SPECT imaging. Various characteristics of each candidate compound can be measured, including its affinity and relative selectivity for each types of monoamine transporter. Affinity of a candidate compound relative to that of a radiolabeled standard may be measured with radioreceptor assays. In one method, a radiolabeled marker for a monamine transporter, such as the DAT ligand ($^3$H)WIN 35,428, is incubated with an unlabeled candidate compound and a source of the transporter, such as brain striatum when assessing DAT ligand compounds. The assay is used to identity the concentration of the candidate compound that inhibits half of ($^3$H)WIN 35,428 binding to DAT in a standard concentration of the radiolabeled ligand, often 0.5 nM. That inhibitory concentration, known as the $IC_{50}$ of the candidate compound for that specific radiolabel's binding to the particular transporter in the assay, indicates the affinity of the candidate compound for the transporter. The $IC_{50}$ value of a compound for the norepinephrine transporter typically represents inhibition of half of the binding of a 0.6 nM solution of ($^3$H)nisoxatine to a NET-rich tissue preparation. Similarly, the $IC_{50}$ value for the serotonin transporter represents inhibition of half of the binding either of 0.2 nM ($^3$H)paroxetine or of 1 nM [$^3$H]citalopram to a SERT-rich tissue preparation. The compounds described herein provide molecules with a range of affinities for the various transporters. In some cases, high affinity for a particular transporter is desirable for a given medical need. For example, compounds of the present invention for treating certain SERT-related disorders may be chosen that have an $IC_{50}$ at the SERT of less than about 500 nM or less than about 50 nM. In certain embodiments the compounds have an $IC_{50}$ at the SERT less than about 25 nM, and in some cases, less than about 15 nM.

Selectivity for binding to and inhibition of one transporter over another, such as the SERT relative to the DAT, or vice versa, is another property of tropanes of considerable relevance for development of medications for treating particular monoamine transporter-related disorders while minimizing avoidable side effects. Selective compounds for the present methods exhibit a target:non-target (for example, SERT:DAT or DAT:SERT) selectivity. A compound with high SERT:DAT selectivity might be sought to treat a disorder for which inhibition of serotonin transport is desired with minimal inhibition of dopamine transport. The SERT:DAT selectivity for a particular compound is determined by providing the ratio of the $IC_{50}$ determined in the standard assay for SERT binding affinity to the $IC_{50}$ measured in the assay for DAT binding. If, for example, a compound's $IC_{50}$ for DAT is 1000 nM and for SERT is 2 nM, that compound is 500 fold more selective for SERT than for DAT.

Using the combination of selectivity (ratio of affinities for different transporters). and potency ($IC_{50}$) information for these compounds, one of ordinary skill in the art can readily select the appropriate compound for the desired application in treating SERT, DAT or NET-related disorders.

Pharmaceutical compositions are provided that comprise the compounds of the present invention in a pharmaceutically acceptable carrier. Pharmaceutically acceptable carriers are well known to those skilled in the art. An exemplary pharmaceutical composition is a therapeutically effective amount of a compound of the invention optionally included in a pharmaceutically acceptable and compatible carrier. The term "pharmaceutically-acceptable and compatible carrier" refers to one or more compatible solid or liquid filler diluents or encapsulating substances that are suitable for administration to a human or other animal. The term "compatible" means that the components of the pharmaceutical compositions are capable of being commingled with the compounds of the present invention, and with each other, in a manner such that there is no interaction that would substantially impair the desired pharmaceutical efficacy.

The compounds and preparations of the invention can be administered via intravenous, subcutaneous, transmucosal, transdermal, inhaled, nasal or oral routes. Preparations to be administered by injection may be formulated as a sterile aqueous or non-aqueous solution, suspension or emulsion in association with a pharmaceutically-acceptable parenteral carrier such as physiological saline. In one embodiment, the pharmaceutical composition is a liquid composition in pyrogen-free, sterilized container or vial. The container can be unit dose or multidose.

The term "therapeutically-effective amount" is that amount of the present pharmaceutical compositions which produces a desired result or exerts a desired influence on the particular condition being treated. Various concentrations may be used in preparing compositions incorporating the same ingredient to provide for variations in the age of the patient to be treated, the severity of the condition, the duration of the treatment and the mode of administration. The effective dose will be determined for each condition and patient as is known to those of skill in the art, with reference to such factors as the IC50 of the compound for each transporter, the measured pharmacokinetic properties of the compound, and dose-dependent therapeutic and side effects.

This invention will be illustrated further by the following examples. These examples are not intended to limit the scope of the claimed invention in any manner. The Examples provide suitable methods for preparing compounds of the present invention. However, those skilled in the art may make compounds of the present invention by any other suitable means. As is well known to those skilled in the art, other substituents can be provided for the illustrated compounds by suitable modification of the reactants.

EXAMPLES

A. General Materials and Methods

All exemplified target compounds are analyzed (mp, TLC, CHN, GC and/or HPLC) and characterized ($^1$H-NMR, $^{13}$C-NMR, MS, IR) prior to submission for biological evaluation. The affinity of all the compounds for the DAT, SERT and NET are measured. NMR spectra are recorded on a Bruker 100, a Varian XL 400, or a Bruker 300 NMR spectrometer. Tetramethylsilane ("TMS") is used as internal standard. Melting points are uncorrected and are measured on a Gallenkamp melting point apparatus. Thin layer chromatography (TLC) is carried out on Baker Si 250F plates. Visualization is accomplished with iodine vapor, UV exposure or treatment with phosphomolybdic acid (PMA). Preparative TLC is carried out on Analtech uniplates Silica Gel GF 2000 microns. Flash chromatography is carried out on Baker Silica Gel 40 mM. Elemental Analyses are performed by Atlantic Microlab, Atlanta, Ga. and are within 0.4% of calculated values for each element. A Beckman 1801 Scintillation Counter is used for scintillation spectrometry. 0.1% Bovine Serum Albumin ("BSA") and (–)-cocaine is purchased from Sigma Chemicals. All reactions are conducted under an inert ($N_2$) atmosphere.

$^3$H-WIN 35,428 ($^3$H-CFT, 2β-carbomethoxy-3β-(4-fluorophenyl)-N-$^3$H-methyltropane, 79.4-87.0 Ci/mmol) and $^3$H-citalopram (86.8 Ci/mmol) is purchased from DuPont-New England Nuclear (Boston, Mass.). HPLC analyses are carried out on a Waters 510 system with detection at 254 nm on a Chiralcel OC column (flow rate: 1 mL/min).

B. Synthesis of Compounds

The compounds of the present invention can be made as either an E or a Z configuration or a mixture of E and Z. The compounds can be either (1R), (1S) or a racemic mixture of (1RS). The following procedures are illustrative examples of how these compounds are synthesized. The method can be used to synthesize any 8-X compounds, where X can be any of the following: N, O, S. $CH_2$, or others as described herein. The synthesis of the 6- or 7-substituted derivatives may also be synthesized in this manner with R at the 6- or 7-position being taken as that described herein. In the case of 6- or 7-hydroxyl (OH) then an appropriate protecting group such as a MOM-protect group should be used. (see e.g., U.S. Pat. No. 5,948,933, incorporated herein in its entirety.)

Example B1

Figure 1:
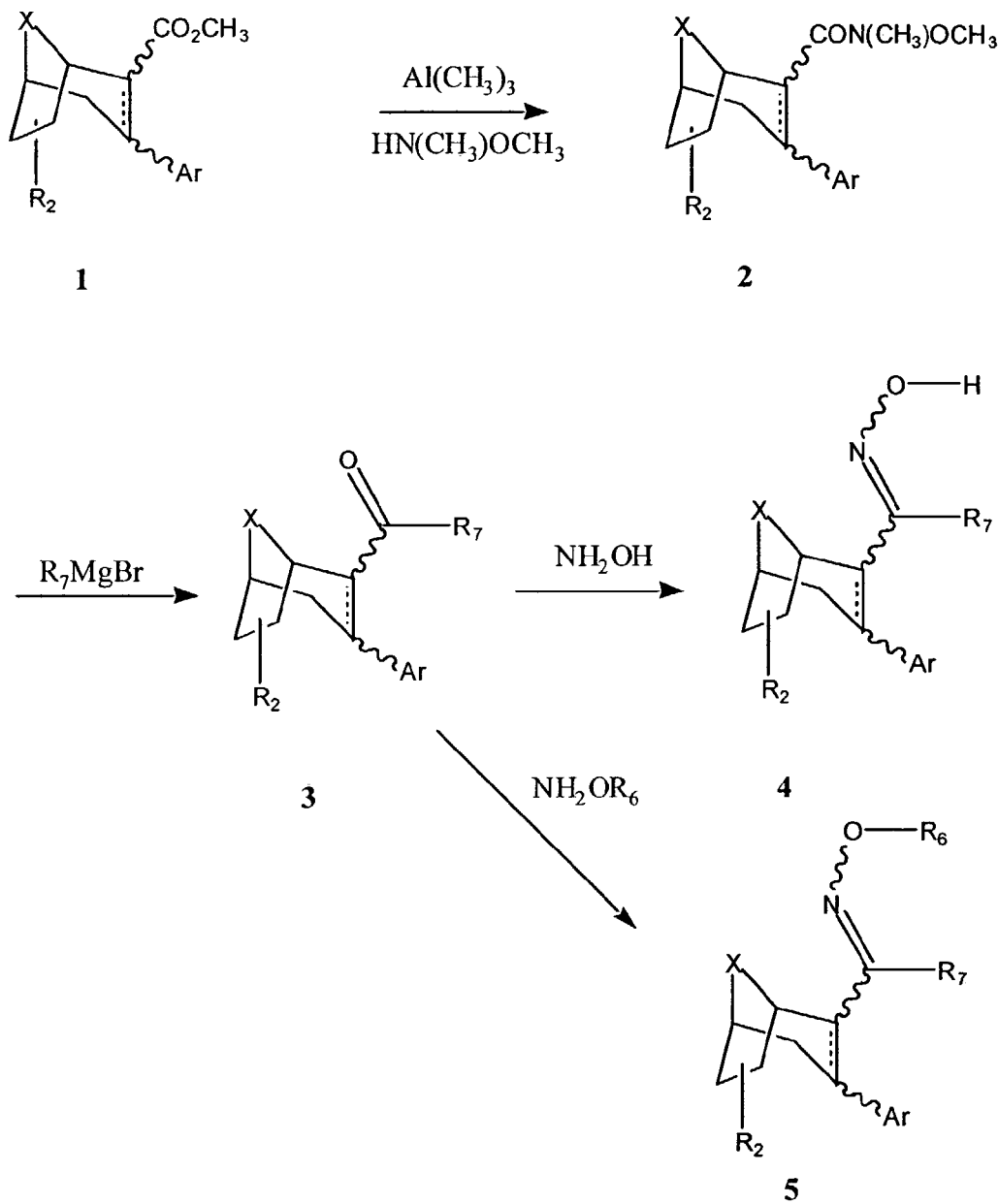
FIG. 1 shows a reaction scheme to obtain the compounds of the present invention (Scheme 1).
Figure 2:
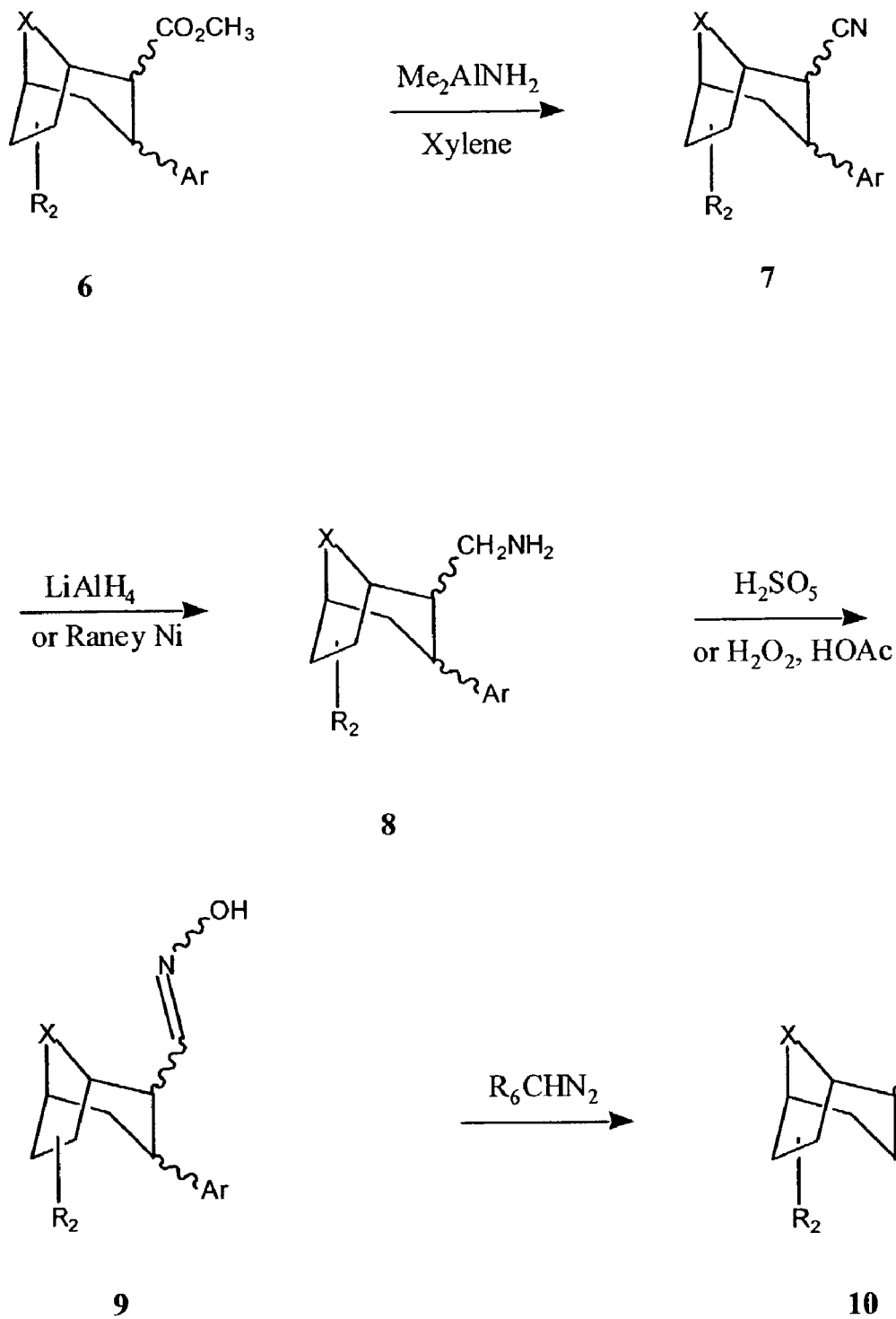
FIG. 2 shows another reaction scheme to obtain the compounds of the present invention (Scheme 2).
Figure 3:
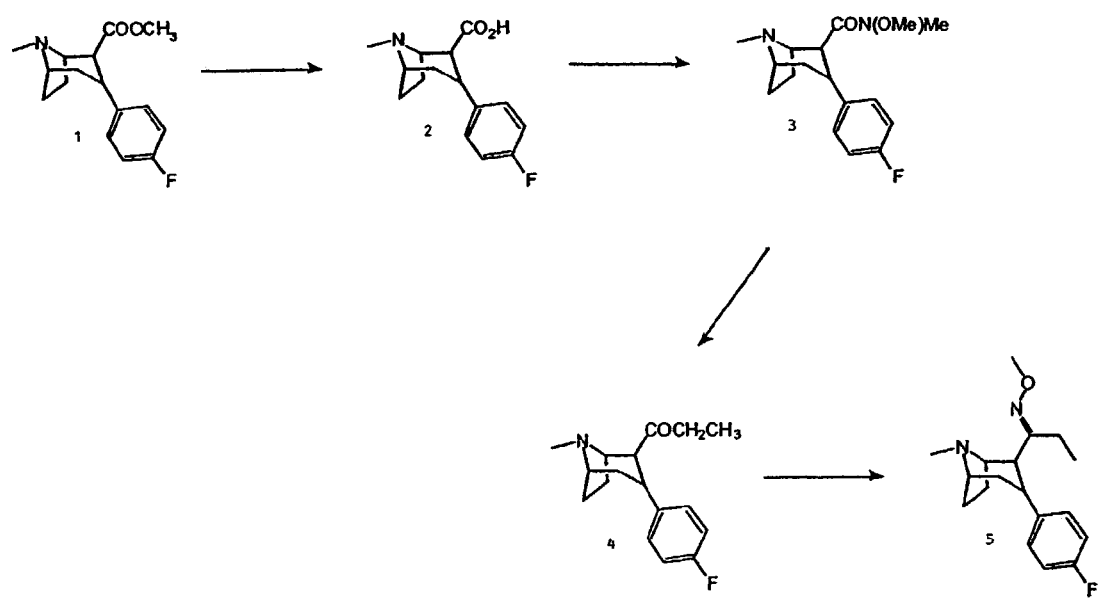
FIG. 3 shows another reaction scheme to obtain the compounds of the present invention (Scheme 3).

Synthesis of 1-[3-(4-Fluoro-phenyl)-8-methyl-8-aza-bicyclo[3.2.1]oct-2-yl]-propan-1-one O-methyl-oxime (5) (FIG. 3)

This method can be used to synthesize boat compounds (Ar is 3-alpha) and chair compounds (Ar is 3-beta) and the 6- or 7-substituted compounds (6-alpha or 6-beta or 7-alpha or 7-beta). This method can also be used to synthesize compounds with different $R_6$ groups by changing the methyl-hydroxyl-amine. Thus, to synthesize $R_6$=H, hydroxylamine is used, for $R_6$=ethyl, ethyl-hydroxyl-amine is used, etc.

2β-Carboxy-3β-(4-fluorophenyl) Tropane, 2

2β-Carbomethoxy-3β-(4-fluorophenyl)tropane (WIN 35,428) (1), is boiled for 24 h in a 1:1 dioxane-water solution. The solvent is removed in vacuo and the residue is almost completely dissolved in $CHCl_3$. Remaining undissolved solid can then be filtered off, toluene can then be added, and the volume of the solution is reduced in vacuo to approximately 25%. Cooling the resulting white suspension in a freezer for 2 h will provide a precipitated solid which can then be isolated by filtration and is washed with cold 1:1 $CHCl_3$-toluene. The solid can then be pumped dry to give the product.

2β-Carboxylic Acid Methoxy Methyl Amide-3β-(4-fluorophenyl)tropane, 3

To a stirred suspension of the acid in anhydrous DCM containing DMF is added oxalyl chloride dropwise which should result in copious bubbling and dissolution of the suspension. The reaction can then be allowed to stir for 45 min during which time the solution will become yellow. The solution can then be reduced in vacuo and pumped at high vacuum overnight, care should be taken to bleed nitrogen into the evacuated flask when it is transfered from the rotary to the pump.

To the acid chloride dissolved in DCM is added (MeO)MeNH HCl. The reaction can then be allowed to stir for 1 h and is partitioned across $CHCl_3$ and 2M $Na_2CO_3$. The aqueous layer can then be extracted with $CHCl_3$ and then the combined organics is dried over $Na_2SO_4$, filtered and reduced in vacuo to provide a yellow solid. This crude product can then be dissolved in DCM and purified by flash chromatography. The product containing fractions is combined and concentrated to give the product.

2β-(1-Propanoyl)-3β-(4-fluorophenyl) Tropane, 4

A solution of 2β-carboxylic acid methoxy methyl amide-3β-(4-fluorophenyl)tropane in THF is cooled to 0° C. and then a Grignard such as $EtMgBr/Et_2O$ is added dropwise over 4 min. The reaction can then be warmed to room temperature for 30 min and then heated to 65° C. for 45 min. The mixture can then be cooled to 0° C. and quenched by addition of ethereal HCl. The resulting cloudy solution can then be basified with 2M $Na_2CO_3$. Ether (5 mL) can then be added and the layers is separated and the aqueous layer washed with $Et_2O$ and $CHCl_3$. The combined organic extracts is dried over $Na_2SO_4$, filtered and concentrated. The product is purified by flash column chromatography to provide the pure ketone.

The above experimental has been described in U.S. Ser. No. 09/568,106, incorporated herein in its entirety.

1-[3-(4-Fluoro-phenyl)-8-methyl-8-aza-bicyclo[3.2.1]oct-2-yl]-propan-1-one O-methyl-oxime, 5

The ketone, 2β-(1-Propanoyl)-3β-(4-fluorophenyl)tropane, is dissolved in an appropriate organic solvent such as methanol and then at room temperature the desired alkyl-hydroxyl-amine, such as methyl-hydroxyl-amine, is added in excess (1.01 to 10 equivalents but preferably 5 equivalents). This amine is added as its hydrochloride or as a free base. If a salt is used such as a hydrochloride then an equivalent amount of mild base should be added, such as potassium bicarbonate or other equivalent salt in order to neutralize the amine hydrochloride. If necessary the solution is boiled until reaction occurs, typically 15 minutes to 24 hours is needed. The desired oxime, 1-[3-(4-Fluoro-phenyl)-8-methyl-8-aza-bicyclo[3.2.1]oct-2-yl]-propan-1-one O-methyl-oxime is isolated as an E, Z-mixture and if so desired separated by flash silica gel chromatography to provide either the pure E or pure Z-compound. The pH of the reaction solution is most preferably about 4 but may range from 1-12. See, for example, Morgan et al. *J. Am. Chem. Soc.* 1994, 116(8),3251-3260.

Example B2

Figure 5:
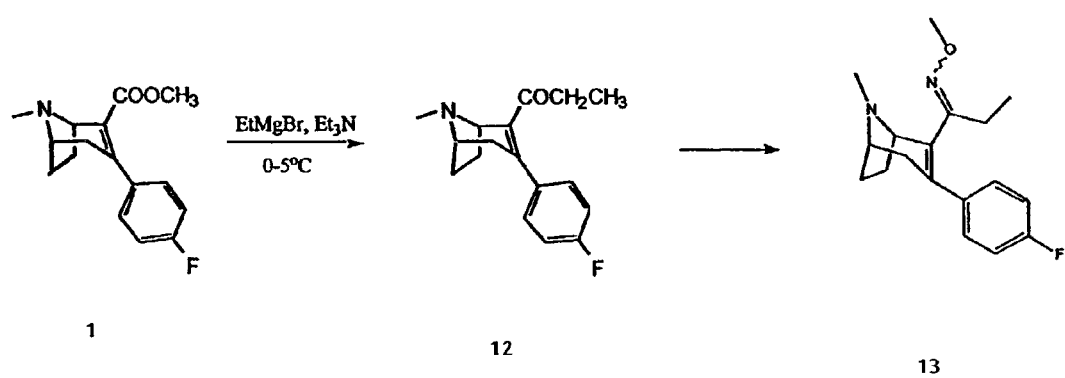
FIG. 5 shows another reaction scheme to obtain the compounds of the present invention (Scheme 5).

Synthesis of (1R and/or 1S)-1-[3-(4-Fluoro-phenyl)-8-methyl-8-aza-bicyclo[3.2.1]oct-2-en-2-yl]-propan-1-one O-methyl-oxime, 13 (FIG. 5)

The example below is for the ethyl group as $R_7$ and the methyl group as $R_6$ and X=NCH$_3$ and $R_5$ as H and Ar as 4-fluorophenyl. This method is used to make boat compounds (where Ar is 3-alpha) and the chair compounds (where Ar is 3-beta) and the 6- or 7-substituted compounds (6-alpha or 6-beta or 7-alpha or 7-beta). This method can also apply for different $R_6$-groups by changing the methyl-hydroxyl-amine. Thus for $R_6$=H, hydroxylamine is used, for $R_6$=ethyl, ethyl-hydroxyl-amine is used, etc.

(1R and/or 1S)-1-[3-(4-Fluoro-phenyl)-8-methyl-8-aza-bicyclo[3.2.1]oct-2-en-2-yl]-propan-1-one (12)

To a solution of the ene-ester (1) in THF is added Et$_3$N (dried over KOH) and then this solution is cooled to 5-10° C. under nitrogen. Ethylmagnesium bromide (3M in diethyl-ether, 1-10 equivalents but most preferably 5.4 equivalents) can then be added dropwise to the reaction solution. This reaction mixture should be stirred at 5-10° C. for 1-10 hours and then is quenched with HCl (4N) aqueous solution. This reaction mixture should then be diluted with water and have the pH adjusted to about 8-9. This mixture can then be extracted with DCM. The DCM layers can then be combined, washed with water, dried over K$_2$CO$_3$, filtered and concentrated and should provide the product. The crude product is further purified by flash chromatography (silica gel) to give the desired ene-keto-compound.

(1R and/or 1S)-1-[3-(4-Fluoro-phenyl)-8-methyl-8-aza-bicyclo[3.2.1]oct-2-en-2-yl]-propan-1-one O-methyl-oxime (13)

The ketone is dissolved in an appropriate organic solvent such as methanol and then at room temperature the desired alkyl-hydroxyl-amine, such as methyl-hydroxyl-amine, is added in excess (1.01 to 10 equivalents but preferably 5 equivalents). This amine is added as its hydrochloride or as a free base. If a salt is used such as a hydrochloride then an equivalent amount of mild base should be added, such as potassium bicarbonate or other equivalent salt in order to neutralize the amine hydrochloride. If necessary the solution is boiled until reaction occurs, typically 15 minutes to 24 hours is needed. The desired oxime, 1-[3-(4-fluoro-phenyl)-8-methyl-8-aza-bicyclo[3.2.1]oct-2-yl]-propan-1-one O-methyl-oxime is isolated as an E, Z-mixture and if so desired separated by flash silica gel chromatography to provide either the pure E or pure Z-compound. The pH of the reaction solution is most preferably about 4 but may range from 1-12. Alpha beta unstaturated oximes have been prepared in this manner before in the literature. For example: Sheikh et al. *Can. J. Chem.* 1972, 50, 2776-2785.

Example B3

Figure 4:
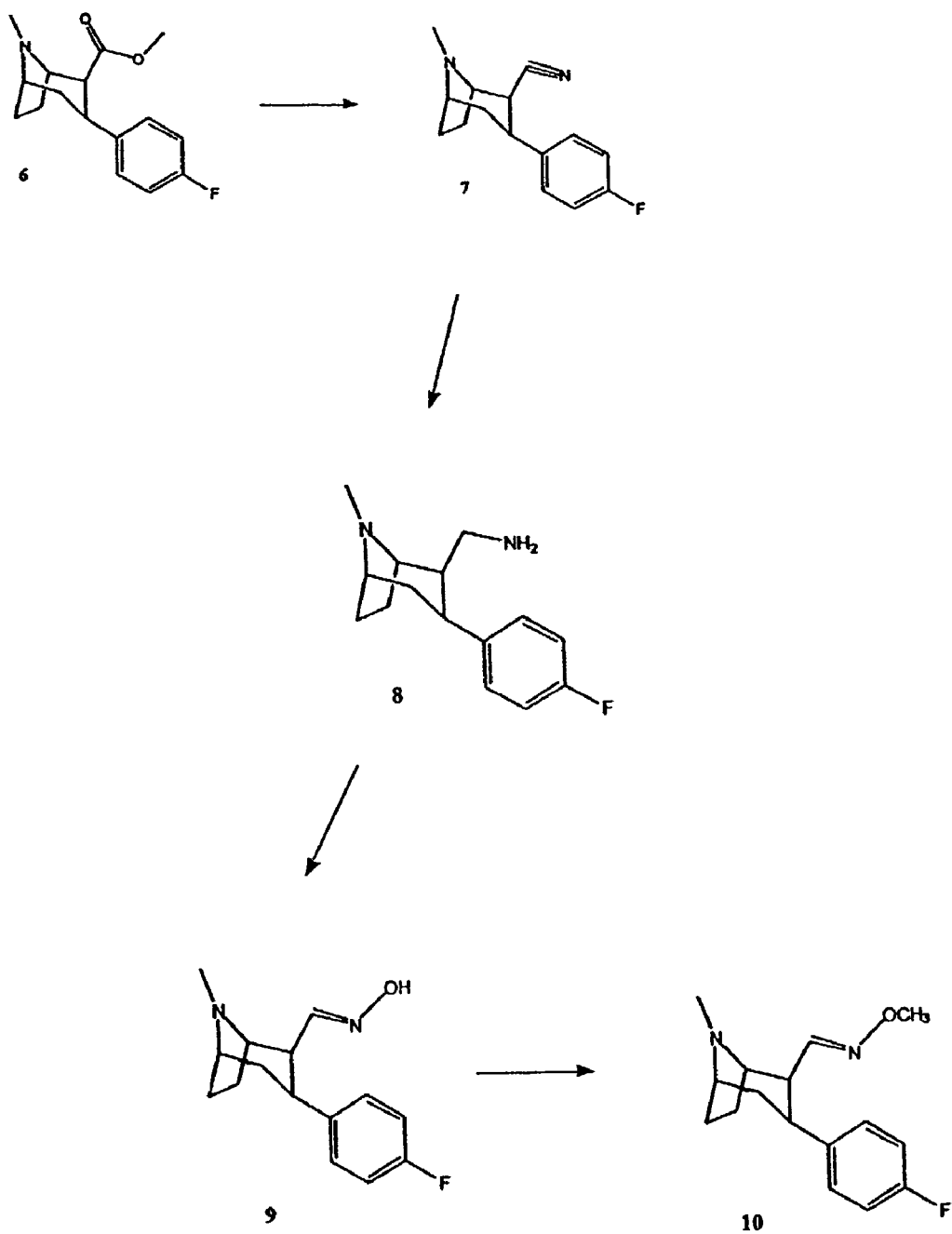
FIG. 4 shows another reaction scheme to obtain the compounds of the present invention (Scheme 4).

Synthesis of (1R and/or 1S)-3-(4-fluoro-phenyl)-8-methyl-8-aza-bicyclo[3.2.1]octane-2-carbaldehyde O-methyl-oxime (FIG. 4)

The example below is for the methyl group as $R_6$ and X=NCH$_3$ and $R_2$ as H and Ar as 4-fluorophenyl. This method is used to make boat compounds (where Ar is 3-alpha) and the chair compounds (where Ar is 3-beta) and the 6- or 7-substituted compounds (6-alpha or 6-beta or 7-alpha or 7-beta). This experimental can also apply for different $R_6$-groups by changing the diazomethane to a diazoalkane (or diazoakene etc.) Thus for $R_6$=H, diazomethane hydroxylamine is used, for $R_6$=ethyl, diazoethane is used etc.

(1R and/or 1S)-3-(4-fluoro-phenyl)-8-methyl-8-aza-bicyclo[3.2.1]octane-2-carbonitrile (7)

To a solution of the ester (3-(4-fluoro-phenyl)-8-methyl-8-aza-bicyclo[3.2.1]octane-2-carboxylic acid methyl ester) in dry xylene is added dimethylaluminum amide in DCM. The mixture can then be heated to a rolling boil for 0.5-19 hours until TLC indicates that complete reaction has occurred. The mixture can then be cooled and water is added. The layers should be separated and the organic phase dried and concentrated. The crude product should be isolated by flash silica gel column chromatography. See e.g., Wood et al. *Tetrahedron Letters* 1979, 51, 4907-4910.

(1R and/or 1S)-C-[3-(4-fluoro-phenyl)-8-methyl-8-aza-bicyclo[3.2.1]oct-2-yl]-methylamine (8)

The nitrile obtained above 3-(4-fluoro-phenyl)-8-methyl-8-aza-bicyclo[3.2.1]octane-2-carbonitrileketone, is dissolved in an appropriate organic solvent such as THF and then this solution is cooled. To this solution should be added lithium aluminum hydride (excess or one equivalent) either neat or as a solution in THF or some other inert solvent. The cold solution should be stirred until the reduction is complete 0.5-15. hours (TLC or other means such as MS or NMR). If needed the solution may be boiled. Once the reaction is complete then water is added very cautiously. The reaction solution can then be partitioned between an organic solvent such as dichloromethane and a saturated solution of sodium bicarbonate or another mild base or just water. The organic phase is then be isolated and dried. The pure desired amine is isolated by flash silica gel column chromatography.

(1R and/or 1S)-3-(4-fluoro-phenyl)-8-methyl-8-aza-bicyclo[3.2.1]octane-2-carbaldehyde Oxime (9)

The amine obtained above C-[3-(4-fluoro-phenyl)-8-methyl-8-aza-bicyclo[3.2.1]oct-2-yl]-methylamine is oxidized with either Caro's acid (H$_2$SO$_5$) or hydrogen peroxide in acetic acid to provide the desired oxime. Thus the amine is dissolved in acetic acid and then the solution is cooled and then hydrogen peroxide can then be added (hydrogen peroxide 5-50% in water). The reaction mixture is monitored by TLC or other methods. When the reaction is complete then the reaction mixture is partitioned between an organic solvent such as dichloromethane and washed with sodium carbonate or other base such as 1 M sodium hydroxide (until the pH is between 8-10) and then sodium thiosufate. The organic phase is dried and concentrated. The pure product is used as is or purified by crystallization. See e.g., Kahr et al. *Chem. Ber.*, 1960, 93, 132.

(1R and/or 1S)-3-(4-fluoro-phenyl)-8-methyl-8-aza-bicyclo[3.2.1]octane-2-carbaldehyde O-methyl-oxime (10)

The carbaldehyde-oxime obtained above is converted to an alkyl oxime by treatment with a diazoalkane such as diazomethane. Thus 3-(4-fluoro-phenyl)-8-methyl-8-aza-bicyclo[3.2.1]octane-2-carbaldehyde oxime is dissolved in an appropriate alcohol such as methanol or ethanol or an organic solvent such as ethyl acetate and then this solution is cooled in an ice/water bath and then a solution of diazomethane. (excess 1.1-20 equivalents) is added. The reaction mixture should be stirred until the reaction is complete (TLC) and then the desired product isolated by solvent evaporation. The pure product is obtained by crystallization or flash column chromatography.

C. Synthesis of Prodrug Ester Compounds

Figure 9:
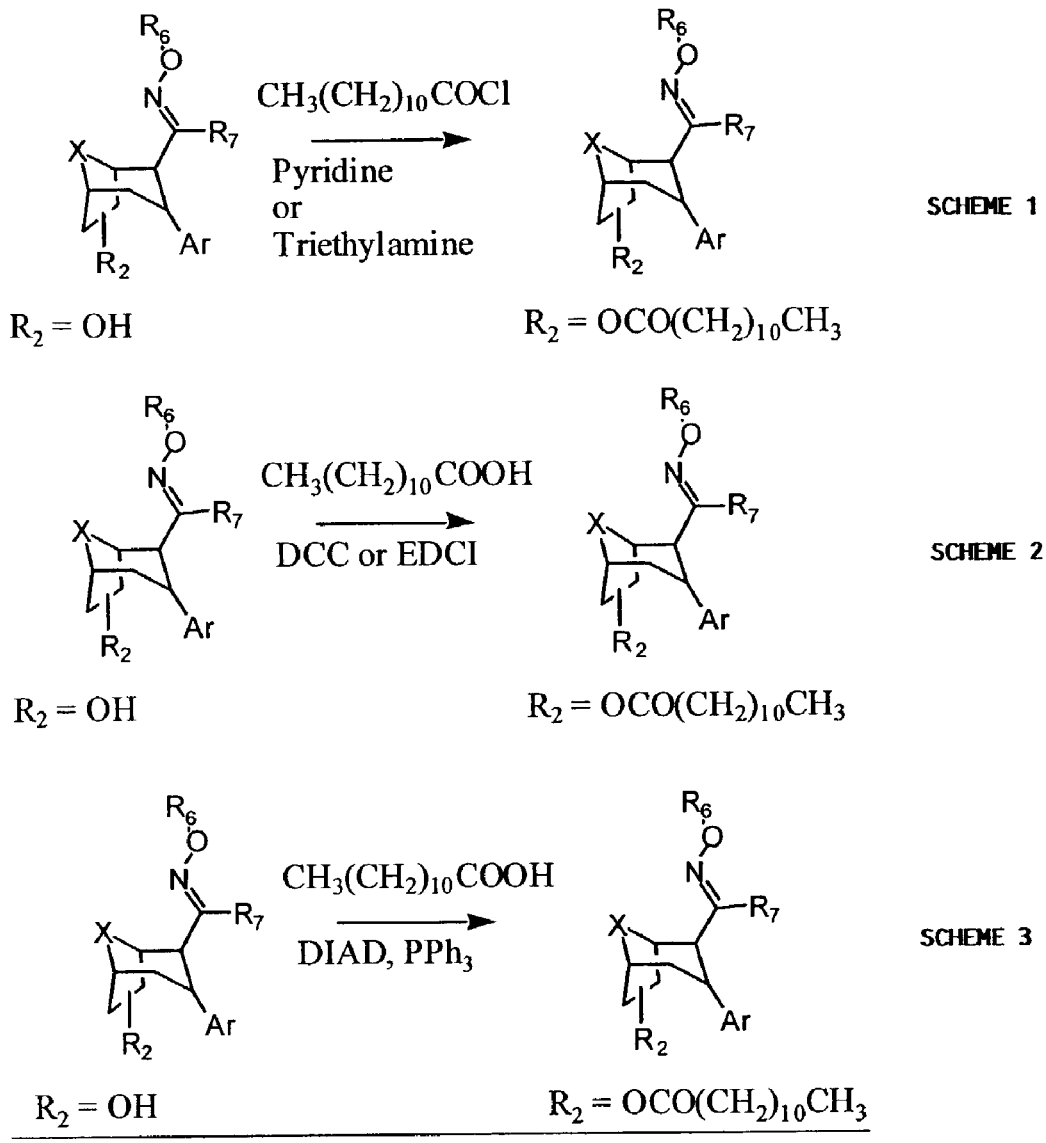
FIG. 9 shows three schemes for synthesizing the prodrug ester compounds from their respective alcohols.

The prodrug ester compounds can be synthesized from their respective alcohols $R_2$=OH to their respective esters. FIG. 9 shows three general means of synthesizing esters from alcohols. However, other methods are known in the art for this transformation and the examples shown are not to limit the method of synthesis.

Scheme 1 shows a synthesis involving dodecanoyl chloride and triethylamine. Thus the tropane alcohol is dissolved in an inert organic solvent such as dichloromethane (DCM) and then the base such as triethylamine is added and the solution can be cooled if necessary. To this cold solution is then added the acid chloride such as dodecanoyl chloride either as a solution in dichloromethane or neat and the resulting mixture is stirred until the reaction is complete. The reaction is then partitioned between water and dichloromethane and the phases separated. The organic phase should be dried, filtered and concentrated. Purification can be achieved by either crystallization or silica gel column chromatography.

Scheme 2 shows the ester formation using either 1,3-dicyclohexylcarbodiimide (DCC) or 1-(3-dimethylaminopropyl)-3-ethylcarbodiimide hydrochloride (EDCI) and dodecanoic acid. Thus the alcohol and the acid are dissolved in a suitable organic solvent such as dichloromethane or THF and then the carbodiimide (DCC or EDCI) dissolved in DCM or THF is added dropwise to the acid/alcohol solution and the reaction is stirred until ester formation is complete by TLC or other analytical means. The reaction is then partitioned between water and dichloromethane and the phases separated. The organic phase should be dried, filtered and concentrated. Purification can be achieved by either crystallization or silica gel column chromatography.

Scheme 3 shows the ester formation using diisopropyl azodicarboxylate (DIAD) and triphenylphosphine and dodecanoic acid. Thus the alcohol and the acid (dodecanoic acid in this case) and triphenylphosphine are dissolved in a suitable organic solvent such as dichloromethane or THF and then the DIAD neat or dissolved in either DCM or THF is added dropwise to the acid/alcohol/$PPh_3$ solution and the reaction is stirred until ester formation is complete by TLC or other analytical means. The reaction is then partitioned between water and dichloromethane and the phases separated. The organic phase should be dried, filtered and concentrated. Purification can be achieved by either crystallization or silica gel column chromatography. This method allows inversion of the stereochemistry at the alcohols position (alpha to beta or beta to alpha).

D. Dopamine Transfer Assay.

The dopamine transporter is labeled with $^3$H-WIN 35,428 (70-85 Ci/mmol, DuPont-NEN). The affinity of novel compounds for the dopamine transporter will be determined in experiments by incubating tissue with a fixed concentration of $^3$H-WIN 35,428 and a range of concentration of the compound as previously described. Madras et al., (1989), *Mol. Pharmacol.* 36: 518-524. Stock solutions are diluted serially in the assay buffer and added (0.2 mL) to the assay medium. The assay tubes receive, in Tris.HCl buffer (50 mM, pH 7.4 at 0-4° C.; NaCl 100 mM), the following constituents at a final assay concentration: drug (0.2 ml; 1 pM-300 µM, depending on affinity), $^3$H-WIN 35,428 (0.2 ml; 0.3. or 1 nM); membrane preparation (0.2 ml; 1-4 mg original wet weight of tissue/ml), depending on the assay. The 2 h incubation (0-4° C.) is initiated by addition of membranes and terminated by rapid filtration over Whatman GF/B glass fiber filters pre-soaked in 0.1% bovine serum albumin (Sigma Chem. Co.). The filters are washed twice with 5 ml Tris.HCl buffer (50 mM), incubated overnight at 0-4° C. in scintillation fluor (Beckman Ready-Value, 5 ml) and radioactivity (dpm) is measured by liquid scintillation spectrometry (Beckman 1801). Total binding is defined as $^3$H-WIN 35,428 bound in the presence of ineffective concentrations of the drug. Non-specific binding is defined as $^3$H-WIN 35,428 bound in the presence of an excess (30 µM) of (−)-cocaine or mazindol (1 µM). Specific binding is the difference between the two values.

E. Serotonin Transporter Assay.

The serotonin transporter is labeled by $^3$H-citalopram (specific activity 82 Ci/mmol, DuPont-NEN). The serotonin transporter is assayed in caudate-putamen membranes using conditions similar to those for the dopamine transporter. The serotonin transporter is expressed at relatively high density in the caudate-putamen (20 pmol/g) and the affinity of $^3$H-citalopram is approximately 2 nM. Drug affinities are determined by incubating tissue with a fixed 1 nM concentration of $^3$H-citalopram and a range of concentrations of the test compounds. The assay tubes receive, in Tris.HCl buffer (50 mM, pH 7.4 at 0-4° C.; NaCl 100 mM), the following constituents at a final assay concentration: drug (0.2 ml of various concentrations); $^3$H-citalopram (0.2 ml; 1 nM); and membrane preparation (0.2 ml; 4 mg original wet weight of tissue/ml). The 2 h incubation (0-4° C.) is initiated by addition of membranes and terminated by rapid filtration over Whatman GF/B glass fiber filters pre-soaked in 0.1% polyethyleneimine. The filters are washed twice with 5 ml Tris.HCl buffer (50 mM) and the remaining steps are carried out as described above. Total binding is defined as $^3$H-citalopram bound in the presence of ineffective concentrations of unlabeled citalopram (1 pM) or the test compounds. Non-specific binding is defined as $^3$H-citalopram bound in the presence of an excess (10 µM) of fluoxetine. Specific binding is the difference between the two values.

F. Norepinephrine Transporter Assay.

Binding properties of compounds to the norepinephrine transporter (NET) are assayed in thalamic tissue, which has a high density of the NET, and is measured using assay conditions similar to those used to measure SERT binding properties (Madras et al., *Synapse* 22:239-246, 1996). The affinity for the norepinephrine transporter of each test compound relative to that of $^3$H-nisoxetine is determined in experiments by incubating thalamic tissue with a fixed concentration of $^3$H-nisoxetine (specific activity 74 Ci/mmol, DuPont-NEN). and a range of concentrations either of unlabeled compound or of unlabeled nisoxetine. The assay tubes receive the following constituents at a final assay concentration: nisoxetine or drug (0.2 ml; 1 pM-300 µM), $^3$H-nisoxetine (0.2 ml; 0.6 nM); and membrane preparation (0.2 ml; 4 mg original wet weight of tissue/ml). The buffer in the assay medium is Tris.HCl 50 mM, pH 7.4 at 0-4° C.; NaCl 300 mM. The 16 h incubation at 0-4° C. is initiated by addition of membranes and terminated by rapid filtration over Whatman GF/B glass fiber filters pre-soaked in 0.1% polyethyleneimine. The remaining steps are as described above. Total binding is defined as $^3$H-nisoxetine bound in the absence of unlabeled NET ligand compounds. Non-specific binding is defined as $^3$H-nisoxetine bound in the presence of an excess (10 µM) of desipramine. Specific binding is the difference between the two values.

G. Data Analysis.

Data are analyzed by EBDA and LIGAND computer software (Elsevier-Biosoft, UK) Final estimates of $IC_{50}$ and nH values are computed by the EBDA program. Baseline values for the individual drugs are established by computer analysis using the baseline drugs as guide. The LIGAND program provides final parameter estimates of the novel compounds by iterative non-linear curve-fitting and evaluation of one- or two-component binding models.

H. Examples of Compounds:

The following tables list examples of compounds of the present invention. In these Tables, the generic name is given for the group of compounds and some of the possible substituents at each position are listed. Thus, the compound can be any combination of the groups listed and can be selected by one of ordinary skill in the art based on the teachings disclosed herein.

TABLE 1

(1R and/or 1S)-8-Aza-compounds (X = $NR_3$)
Generic name: (1R and/or 1S)-1-[3-(Aryl)-6-alkoxy-8-alkyl-8-aza-bicyclo[3.2.1]oct-2-yl]-alkyl-1-one O-alkyl-oxime or (1R and/or 1S)-1-[3-(Ar)-6-$R_2$-8-$R_3$-8-aza-bicyclo[3.2.1] oct-2-yl]-$R_7$-1-one O-$R_6$-oxime, where:

| 3-alpha or beta Ar = | 6-or 7- alpha or beta $R_2$ | 8-$R_3$ | 2-alpha or beta $R_7$ | E and/or Z $OR_6$ |
|---|---|---|---|---|
| 4-Fluorophenyl | Hydroxy | H | H | H |
| 3,4-Dichlorophenyl | Methoxy | Methyl | Methyl | Methyl |
| 2-Naphthyl | Ethoxy | Ethyl | Ethyl | Ethyl |
| 3,4-Diacetoxyphenyl | Acetoxy | 3-Phenylpropyl | Propyl | Propyl |
| 4,4'-Difluorodiphenyl-methoxy | Dodecyloxy | Benzyl | Phenyl | Phenyl |
| 3-Iodo-4-isopropenyl | Dodecanoyloxy | Propyl | Benzyl | 3-Phenylpropyl |
| 3-Bromo-4-isopropenyl | Butyryloxy | 5-Phenylpentyl | | Allyl |
| 3,4-Dihydroxyphenyl | Pentanoyloxy | Iodoallyl | | Iodoallyl |
| 4,-Fluoro-4'-methyl-diphenylmethoxy | Octanoyloxy | Fluoroallyl | | Fluoroallyl |
| 4,4'-Dichlorodiphenyl-methoxy | Palmitoyloxy | Allyl | | 5-Phenylpentyl |
| 4,-Fluoro-4'-chloro-diphenyl-methoxy | Stearoyloxy | | | Benzyl |
| 4,4'-Dimethyldiphenyl-methoxy | Arachidoyloxy | | | |
| 4-Fluoro-diphenyl-methoxy | Lignoceroyloxy | | | |
| 4-Iodophenyl | Palmitoleoyloxy | | | |
| 4-Isopropenyl | Oleoyloxy | | | |
| | Hydrogen | | | |

An example of such a compound is (1R and/or 1S)-1-[3-(3,4-Dichloro-phenyl)-6-hydroxy-8-methyl-8-aza-bicyclo[3.2.1]oct-2-yl]-propan-1-one O-methyl-oxime.

TABLE 2

(1R and/or 1S)-8-Oxa-compounds (X = O)
Generic name: (1R and/or 1S)-1-[3-(Aryl)-6-alkoxy-8-oxa-bicyclo[3.2.1]oct-2-yl]-alkyl-1-one O-alkyl-oxime or (1R and/or 1S)-1-[3-(Ar)-6-$R_2$-8-oxa-bicyclo[3.2.1] oct-2-yl]-$R_7$-1-one O-$R_6$-oxime, Where:

| 3-alpha or beta Ar = | 6-or 7- alpha or beta $R_2$ | 2-alpha or beta $R_7$ | E and/or Z $OR_6$ |
|---|---|---|---|
| 4-Fluorophenyl | Hydroxy | H | H |
| 3,4-Dichlorophenyl | Methoxy | Methyl | Methyl |
| 2-Naphthyl | Ethoxy | Ethyl | Ethyl |
| 3,4-Diacetoxyphenyl | Acetoxy | Propyl | Propyl |
| 4,4'-Difluorodiphenyl-methoxy | Dodecyloxy | Phenyl | Phenyl |
| 3-Iodo-4-isopropenyl | Dodecanoyloxy | Benzyl | 3-Phenylpropyl |
| 3-Bromo-4-isopropenyl | Butyryloxy | | Allyl |
| 3,4-Dihydroxyphenyl | Pentanoyloxy | | Iodoallyl |
| 4,-Fluoro-4'-methyl-diphenylmethoxy | Octanoyloxy | | Fluoroallyl |
| 4,4'-Dichlorodiphenyl-methoxy | Palmitoyloxy | | 5-Phenylpentyl |
| 4,-Fluoro-4'-chloro-diphenyl-methoxy | Stearoyloxy | | Benzyl |
| 4,4'-Dimethyldiphenyl-methoxy | Arachidoyloxy | | |
| 4-Fluoro-diphenyl-methoxy | Lignoceroyloxy | | |
| 4-Iodophenyl | Palmitoleoyloxy | | |
| 4-Isopropenyl | Oleoyloxy | | |
| | Hydrogen | | |

An example of such a compound is (1R and/or 1S)-1-[3-(3, 4-Dichloro-phenyl)-6-hydroxy-8-oxa-bicyclo[3.2.1]oct-2-yl]-propan-1-one O-methyl-oxime.

TABLE 3

(1R and/or 1S)-8-Carba-compounds (X = C)
Generic name: (1R and/or 1S)-1-[3-(Aryl)-6-alkoxy-bicyclo[3.2.1] oct-2-yl]-alkyl-1-one O-alkyl-oxime or (1R and/or 1S)-1-[3-(Ar)- 6-$R_2$-bicyclo[3.2.1 2-yl]-$R_7$-1-one O-$R_6$-oxime, Where

| 3-alpha or beta Ar = | 6-or 7- alpha or beta $R_2$ | 2-alpha or beta $R_7$ | E and/or Z O$R_6$ |
|---|---|---|---|
| 4-Fluorophenyl | Hydroxy | H | H |
| 3,4-Dichlorophenyl | Methoxy | Methyl | Methyl |
| 2-Naphthyl | Ethoxy | Ethyl | Ethyl |
| 3,4-Diacetoxyphenyl | Acetoxy | Propyl | Propyl |
| 4,4'-Difluorodiphenyl-methoxy | Dodecyloxy | Phenyl | Phenyl |
| 3-Iodo-4-isopropenyl | Dodecanoyloxy | Benzyl | 3-Phenylpropyl |
| 3-Bromo-4-isopropenyl | Butryloxy | | Allyl |
| 3,4-Dihydroxyphenyl | Pentanoyloxy | | Iodoallyl |
| 4,-Fluoro-4'-methyl-diphenylmethoxy | Octanoyloxy | | Fluoroallyl |
| 4,4'-Dichlorodiphenyl-methoxy | Palmitoyloxy | | 5-Phenylpentyl |
| 4,-Fluoro-4'-chloro-diphenyl-methoxy | Stearoyloxy | | Benzyl |
| 4,4'-Dimethyldiphenyl-methoxy | Arachidoyloxy | | |
| 4-Fluoro-diphenyl-methoxy | Lignoceroyloxy | | |
| 4-Iodophenyl | Palmitoleoyloxy | | |
| 4-Isopropenyl | Oleoyloxy Hydrogen | | |

An example of such a compound includes: (1R and/or 1S)-1-[3-(3,4-Dichloro-phenyl)-6-hydroxy-carba-bicyclo[3.2.1]oct-2-yl]-propan-1-one O-methyl-oxime.

TABLE 4

(1R and/or 1S)-8-Thia-compounds (X = S)
Generic name: (1R and/or 1S)-1-[3-(Aryl)-6-thia-bicyclo[3.2.1] oct-2-yl]-alkyl-1-one O-alkyl-oxime or (1R and/or 1S)-1-[3-(Ar)- 6-$R_2$-8-thia-bicyclo[3.2.1]oct-2-yl]-$R_7$-1-one O-$R_6$-oxime, Where

| 3-alpha or beta Ar = | 6-or 7- alpha or beta $R_2$ | 2-alpha or beta $R_7$ | E and/or Z O$R_6$ |
|---|---|---|---|
| 4-Fluorophenyl | Hydroxy | H | H |
| 3,4-Dichlorophenyl | Methoxy | Methyl | Methyl |
| 2-Naphthyl | Ethoxy | Ethyl | Ethyl |
| 3,4-Diacetoxyphenyl | Acetoxy | Propyl | Propyl |
| 4,4'-Difluorodiphenyl-methoxy | Dodecyloxy | Phenyl | Phenyl |
| 3-Iodo-4-isopropenyl | Dodecanoyloxy | Benzyl | 3-Phenylpropyl |
| 3-Bromo-4-isopropenyl | Butryloxy | | Allyl |
| 3,4-Dihydroxyphenyl | Pentanoyloxy | | Iodoallyl |
| 4,-Fluoro-4'-methyl-diphenylmethoxy | Octanoyloxy | | Fluoroallyl |
| 4,4'-Dichlorodiphenyl-methoxy | Palmitoyloxy | | 5-Phenylpentyl |
| 4,-Fluoro-4'-chloro-diphenyl-methoxy | Stearoyloxy | | Benzyl |
| 4,4'-Dimethyldiphenyl-methoxy | Arachidoyloxy | | |
| 4-Fluoro-diphenyl-methoxy | Lignoceroyloxy | | |
| 4-Iodophenyl | Palmitoleoyloxy | | |
| 4-Isopropenyl | Oleoyloxy Hydrogen | | |

An example of such a compound includes: (1R and/or 1S)-1-[3-(3,4-Dichloro-phenyl)-6-hydroxy-8-thia-bicyclo[3.2.1]oct-2-yl]-propan-1-one O-methyl-oxime.

TABLE 5

(1R and/or 1S)-8-Aza-2,3-ENE compounds (X = N$R_3$)
Generic name: (1R and/or 1S)-1-[3-(Aryl)-6-alkoxy-8-alkyl-8-aza-bicyclo[3.2.1] oct-2-en-2-yl]-alkyl-1-one O-alkyl-oxime or (1R and/or 1S)-1-[3-(Ar)-6-$R_2$-8-$R_3$-8-aza-bicyclo[3.2.1]oct-2-en-2-yl]-$R_7$-1-one O-$R_6$-oxime, Where

| 3-Ar = | 6-or 7-alpha or beta $R_2$ | 8-$R_3$ | 2-$R_7$ | E and/or Z O$R_6$ |
|---|---|---|---|---|
| 4-Fluorophenyl | Hydroxy | H | H | H |
| 3,4-Dichlorophenyl | Methoxy | Methyl | Methyl | Methyl |
| 2-Naphthyl | Ethoxy | Ethyl | Ethyl | Ethyl |
| 3,4-Diacetoxyphenyl | Acetoxy | 3-Phenylpropyl | Propyl | Propyl |
| 4,4'-Difluorodiphenyl-methoxy | Dodecyloxy | Benzyl | Phenyl | Phenyl |
| 3-Iodo-4-isopropenyl | Dodecanoyloxy | Propyl | Benzyl | 3-Phenylpropyl |
| 3-Bromo-4-isopropenyl | Butryloxy | 5-Phenylpentyl | | Allyl |
| 3,4-Dihydroxyphenyl | Pentanoyloxy | Iodoallyl | | Iodoallyl |
| 4,-Fluoro-4'-methyl-diphenylmethoxy | Octanoyloxy | Fluoroallyl | | Fluoroallyl |
| 4,4'-Dichlorodiphenyl-methoxy | Palmitoyloxy | Allyl | | 5-Phenylpentyl |
| 4,-Fluoro-4'-chloro-diphenyl-methoxy | Stearoyloxy | | | Benzyl |
| 4,4'-Dimethyldiphenyl-methoxy | Arachidoyloxy | | | |
| 4-Fluoro-diphenyl-methoxy | Lignoceroyloxy | | | |
| 4-Iodophenyl | Palmitoleoyloxy | | | |
| 4-Isopropenyl | Oleoyloxy Hydrogen | | | |

An example of such a compound includes: (1R and/or 1S)-1-[3-(3,4-Dichloro-phenyl)-6-hydroxy-8-methyl-8-aza-bicyclo[3.2.1]oct-2-en-2-yl]-propan-1-one O-methyl-oxime.

TABLE 6

(1R and/or 1S)-8-Oxa-2,3-ENE compounds (X = O)
Generic name: (1R and/or 1S)-1-[3-(Aryl)-6-alkoxy-8-oxa-bicyclo[3.2.1]oct-2-en-2-yl]-alkyl-1-one O-alkyl-oxime or (1R and/or 1S)-1-[3-(Ar)-6-$R_2$-8-oxa-bicyclo[3.2.1]oct-2-en-2-yl]-$R_7$-1-one O-$R_6$-oxime,
Where

| 3-Ar = | 6-or 7-alpha or beta $R_2$ | 2-$R_7$ | E and/or Z $OR_6$ |
|---|---|---|---|
| 4-Fluorophenyl | Hydroxy | H | H |
| 3,4-Dichlorophenyl | Methoxy | Methyl | Methyl |
| 2-Naphthyl | Ethoxy | Ethyl | Ethyl |
| 3,4-Diacetoxyphenyl | Acetoxy | Propyl | Propyl |
| 4,4'-Difluorodiphenyl-methoxy | Dodecyloxy | Phenyl | Phenyl |
| 3-Iodo-4-isopropenyl | Dodecanoyloxy | Benzyl | 3-Phenylpropyl |
| 3-Bromo-4-isopropenyl | Butyryloxy | | Allyl |
| 3,4-Dihydroxyphenyl | Pentanoyloxy | | Iodoallyl |
| 4,-Fluoro-4'-methyl-diphenylmethoxy | Octanoyloxy | | Fluoroallyl |
| 4,4'-Dichlorodiphenyl-methoxy | Palmitoyloxy | | 5-Phenylpentyl |
| 4,-Fluoro-4'-chloro-diphenyl-methoxy | Stearoyloxy | | Benzyl |
| 4,4'-Dimethyldiphenyl-methoxy | Arachidoyloxy | | |
| 4-Fluoro-diphenyl-methoxy | Lignoceroyloxy | | |
| 4-Iodophenyl | Palmitoleoyloxy | | |
| 4-Isopropenyl | Oleoyloxy | | |
| | Hydrogen | | |

An example of such a compound includes: (1R and/or 1S)-1-[3-(3,4-Dichloro-phenyl)-6-hydroxy-8-oxa-bicyclo[3.2.1]oct-2-en-2-yl]-propan-1-one O-methyl-oxime.

TABLE 7

(1R and/or 1S)-8-Carba-2,3-ENE compounds (X = C)
Generic name: (1R and/or 1S)-1-[3-(Aryl)-6-alkoxy-bicyclo [3.2.1]oct-2-en-2-yl]-alkyl-1-one O-alkyl-oxime or (1R and/or 1S)-1-[3-(Ar)-6-$R_2$-bicyclo[3.2.1]oct-2-en-2-yl]-$R_7$-1-one O-$R_6$-oxime,
Where

| 3-Ar = | 6-or 7-alpha or beta $R_2$ | 2-$R_7$ | E and/or Z $OR_6$ |
|---|---|---|---|
| 4-Fluorophenyl | Hydroxy | H | H |
| 3,4-Dichlorophenyl | Methoxy | Methyl | Methyl |
| 2-Naphthyl | Ethoxy | Ethyl | Ethyl |
| 3,4-Diacetoxyphenyl | Acetoxy | Propyl | Propyl |
| 4,4'-Difluorodiphenyl-methoxy | Dodecyloxy | Phenyl | Phenyl |
| 3-Iodo-4-isopropenyl | Dodecanoyloxy | Benzyl | 3-Phenylpropyl |
| 3-Bromo-4-isopropenyl | Butyryloxy | | Allyl |
| 3,4-Dihydroxyphenyl | Pentanoyloxy | | Iodoallyl |
| 4,-Fluoro-4'-methyl-diphenylmethoxy | Octanoyloxy | | Fluoroallyl |
| 4,4'-Dichlorodiphenyl-methoxy | Palmitoyloxy | | 5-Phenylpentyl |
| 4,-Fluoro-4'-chloro-diphenyl-methoxy | Stearoyloxy | | Benzyl |
| 4,4'-Dimethyldiphenyl-methoxy | Arachidoyloxy | | |
| 4-Fluoro-diphenyl-methoxy | Lignoceroyloxy | | |
| 4-Iodophenyl | Palmitoleoyloxy | | |
| 4-Isopropenyl | Oleoyloxy | | |
| | Hydrogen | | |

An example of such compounds include: (1R and/or 1S)-1-[3-(3,4-Dichloro-phenyl)-6-hydroxy-bicyclo[3.2.1]oct-2-en-2-yl]-propan-1-one O-methyl-oxime.

TABLE 8

(1R and/or 1S)-8-thia-2,3-ENE compounds (X = S)
Generic name: (1R and/or 1S)-1-[3-(Aryl)-6-alkoxy-8-thia-bicyclo[3.2.1]oct-2-en-2-yl]-alkyl-1-one O-alkyl-oxime or (1R and/or 1S)-1-[3-(Ar)-6-$R_2$-8-thia-bicyclo[3.2.1]oct-2-en-2-yl]-$R_7$-1-one O-$R_6$-oxime,
Where

| 3-Ar = | 6-or 7-alpha or beta $R_2$ | 2-$R_7$ | E and/or Z $OR_6$ |
|---|---|---|---|
| 4-Fluorophenyl | Hydroxy | H | H |
| 3,4-Dichlorophenyl | Methoxy | Methyl | Methoxy |
| 2-Naphthyl | Ethoxy | Ethyl | Ethyl |
| 3,4-Diacetoxyphenyl | Acetoxy | Propyl | Propyl |
| 4,4'-Difluorodiphenyl-methoxy | Dodecyloxy | Phenyl | Phenyl |
| 3-Iodo-4-isopropenyl | Dodecanoyloxy | Benzyl | 3-Phenylpropyl |
| 3-Bromo-4-isopropenyl | Butyryloxy | | Allyl |
| 3,4-Dihydroxyphenyl | Pentanoyloxy | | Iodoallyl |
| 4,-Fluoro-4'-methyl-diphenylmethoxy | Octanoyloxy | | Fluoroallyl |
| 4,4'-Dichlorodiphenyl-methoxy | Palmitoyloxy | | 5-Phenylpentyl |
| 4,-Fluoro-4'-chloro-diphenyl-methoxy | Stearoyloxy | | Benzyl |
| 4,4'-Dimethyldiphenyl-methoxy | Arachidoyloxy | | |
| 4-Fluoro-diphenyl-methoxy | Lignoceroyloxy | | |
| 4-Iodophenyl | Palmitoleoyloxy | | |
| 4-Isopropenyl | Oleoyloxy | | |
| | Hydrogen | | |

An example of such compounds includes: (1R and/or 1S)-1-[3-(3,4-Dichloro-phenyl)-6-hydroxy-8-thia-bicyclo[3.2.1]oct-2-en-2-yl]-propan-1-one O-methyl-oxime.

H. Examples of Preferred Compounds:
Table 9 below lists examples of compounds of the present invention.

TABLE 9

(1'R)-1-[3β-(4-Fluoro-phenyl)-7-hydroxy-8-methyl-8-aza-bicyclo[3.2.1]oct-2β-yl]-propan-1-one O-methyl-oxime
(1'R)-1-[7-Hydroxy-3β-(4-iodo-phenyl)-8-methyl-8-aza-bicyclo[3.2.1]oct-2β-yl]-propan-1-one O-methyl-oxime
(1'R)-1-[3β-(3,4-Dichloro-phenyl)-7-hydroxy-8-methyl-8-aza-bicyclo[3.2.1]oct-2β-yl]-propan-1-one O-methyl-oxime
(1'R)-Acetic acid 2-acetoxy-4-[7-hydroxy-2β-(1-methoxyimino-propyl)-8-methyl-8-aza-bicyclo[3.2.1]oct-3β-yl]-phenyl ester
(1'R)-1-(7-Hydroxy-8-methyl-3β-naphthalen-2-yl-8-aza-bicyclo[3.2.1]oct-2β-yl)-propan-1-one O-methyl-oxime

TABLE 9-continued (1'R)-1-{3α-[Bis-(4-fluoro-phenyl)-methoxy]-7-hydroxy-8-methyl-8-aza-bicyclo[3.2.1]oct-2β-yl}-propan-1-one O-methyl-oxime
(1'S)-1-[3β-(4-Fluoro-phenyl)-7-hydroxy-8-methyl-8-aza-bicyclo[3.2.1]oct-2β-yl]-propan-1-one O-methyl-oxime
(1'S)-1-[7-Hydroxy-3β-(4-iodo-phenyl)-8-methyl-8-aza-bicyclo[3.2.1]oct-2β-yl]-propan-1-one O-methyl-oxime
(1'S)-1-[3β-(3,4-Dichloro-phenyl)-7-hydroxy-8-methyl-8-aza-bicyclo[3.2.1]oct-2β-yl]-propan-1-one O-methyl-oxime
(1'S)-Acetic acid 2-acetoxy-4-[7-hydroxy-2β-(1-methoxyimino-propyl)-8-methyl-8-aza-bicyclo[3.2.1]oct-3β-yl]-phenyl ester
(1'S)-1-(7-Hydroxy-8-methyl-3β-naphthalen-2-yl-8-aza-bicyclo[3.2.1]oct-2β-yl)-propan-1-one O-methyl-oxime
(1'S)-1-{3α-[Bis-(4-fluoro-phenyl)-methoxy]-7-hydroxy-8-methyl-8-aza-bicyclo[3.2.1]oct-2β-yl}-propan-1-one O-methyl-oxime
(1'R)-1-[3α-(4-Fluoro-phenyl)-7-hydroxy-8-methyl-8-aza-bicyclo[3.2.1]oct-2β-yl]-propan-1-one O-methyl-oxime
(1'R)-1-[7-Hydroxy-3α-(4-iodo-phenyl)-8-methyl-8-aza-bicyclo[3.2.1]oct-2β-yl]-propan-1-one O-methyl-oxime
(1'R)-1-[3α-(3,4-Dichloro-phenyl)-7-hydroxy-8-methyl-8-aza-bicyclo[3.2.1]oct-2β-yl]-propan-1-one O-methyl-oxime
(1'R)-Acetic acid 2-acetoxy-4-[7-hydroxy-2β-(1-methoxyimino-propyl)-8-methyl-8-aza-bicyclo[3.2.1]oct-3α-yl]-phenyl ester
(1'R)-1-(7-Hydroxy-8-methyl-3α-naphthalen-2-yl-8-aza-bicyclo[3.2.1]oct-2β-yl)-propan-1-one O-methyl-oxime
(1'S)-1-[3α-(4-Fluoro-phenyl)-7-hydroxy-8-methyl-8-aza-bicyclo[3.2.1]oct-2β-yl]-propan-1-one O-methyl-oxime
(1'S)-1-[7-Hydroxy-3α-(4-iodo-phenyl)-8-methyl-8-aza-bicyclo[3.2.1]oct-2β-yl]-propan-1-one O-methyl-oxime
(1'S)-1-[3α-(3,4-Dichloro-phenyl)-7-hydroxy-8-methyl-8-aza-bicyclo[3.2.1]oct-2β-yl]-propan-1-one O-methyl-oxime
(1'S)-Acetic acid 2-acetoxy-4-[7-hydroxy-2β-(1-methoxyimino-propyl)-8-methyl-8-aza-bicyclo[3.2.1]oct-3α-yl]-phenyl ester
(1'S)-1-(7-Hydroxy-8-methyl-3α-naphthalen-2-yl-8-aza-bicyclo[3.2.1]oct-2β-yl)-propan-1-one O-methyl-oxime
(1'R)-1-[3β-(4-Fluoro-phenyl)-7-hydroxy-8-aza-bicyclo[3.2.1]oct-2β-yl]-propan-1-one O-methyl-oxime
(1'R)-1-[7-Hydroxy-3β-(4-iodo-phenyl)-8-aza-bicyclo[3.2.1]oct-2β-yl]-propan-1-one O-methyl-oxime
(1'R)-1-[3β-(3,4-Dichloro-phenyl)-7-hydroxy-8-aza-bicyclo[3.2.1]oct-2β-yl]-propan-1-one O-methyl-oxime
(1'R)-Acetic acid 2-acetoxy-4-[7-hydroxy-2β-(1-methoxyimino-propyl)-8-aza-bicyclo[3.2.1]oct-3β-yl]-phenyl ester
(1'R)-1-(7-Hydroxy-3β-naphthalen-2-yl-8-aza-bicyclo[3.2.1]oct-2β-yl)-propan-1-one O-methyl-oxime
(1'R)-1-{3α-[Bis-(4-fluoro-phenyl)-methoxy]-7-hydroxy-8-aza-bicyclo[3.2.1]oct-2β-yl}-propan-1-one O-methyl-oxime
(1'S)-1-[3β-(4-Fluoro-phenyl)-7-hydroxy-8-aza-bicyclo[3.2.1]oct-2β-yl]-propan-1-one O-methyl-oxime
(1'S)-1-[7-Hydroxy-3β-(4-iodo-phenyl)-8-aza-bicyclo[3.2.1]oct-2β-yl]-propan-1-one O-methyl-oxime
(1'S)-1-[3β-(3,4-Dichloro-phenyl)-7-hydroxy-8-aza-bicyclo[3.2.1]oct-2β-yl]-propan-1-one O-methyl-oxime
(1'S)-Acetic acid 2-acetoxy-4-[7-hydroxy-2β-(1-methoxyimino-propyl)-8-aza-bicyclo[3.2.1]oct-3β-yl]-phenyl ester
(1'S)-1-(7-Hydroxy-3β-naphthalen-2-yl-8-aza-bicyclo[3.2.1]oct-2β-yl)-propan-1-one O-methyl-oxime
(1'S)-1-{3α-[Bis-(4-fluoro-phenyl)-methoxy]-7-hydroxy-8-aza-bicyclo[3.2.1]oct-2β-yl}-propan-1-one O-methyl-oxime
(1'R)-1-[3α-(4-Fluoro-phenyl)-7-hydroxy-8-aza-bicyclo[3.2.1]oct-2β-yl]-propan-1-one O-methyl-oxime
(1'R)-1-[7-Hydroxy-3α-(4-iodo-phenyl)-8-aza-bicyclo[3.2.1]oct-2β-yl]-propan-1-one O-methyl-oxime
(1'R)-1-[3α-(3,4-Dichloro-phenyl)-7-hydroxy-8-aza-bicyclo[3.2.1]oct-2β-yl]-propan-1-one O-methyl-oxime
(1'R)-Acetic acid 2-acetoxy-4-[7-hydroxy-2β-(1-methoxyimino-propyl)-8-aza-bicyclo[3.2.1]oct-3α-yl]-phenyl ester
(1'R)-1-(7-Hydroxy-3α-naphthalen-2-yl-8-aza-bicyclo[3.2.1]oct-2β-yl)-propan-1-one O-methyl-oxime
(1'S)-1-[3α-(4-Fluoro-phenyl)-7-hydroxy-aza-bicyclo[3.2.1]oct-2β-yl]-propan-1-one O-methyl-oxime
(1'S)-1-[7-Hydroxy-3α-(4-iodo-phenyl)-8-methyl-8-aza-bicyclo[3.2.1]oct-2β-yl]-propan-1-one O-methyl-oxime
(1'S)-1-[3α-(3,4-Dichloro-phenyl)-7-hydroxy-8-aza-bicyclo[3.2.1]oct-2β-yl]-propan-1-one O-methyl-oxime
(1'S)-Acetic acid 2-acetoxy-4-[7-hydroxy-2β-(1-methoxyimino-propyl)-8-aza-bicyclo[3.2.1]oct-3α-yl]-phenyl ester
(1'S)-1-(7-Hydroxy-3α-naphthalen-2-yl-8-aza-bicyclo[3.2.1]oct-2β-yl)-propan-1-one O-methyl-oxime
(1'R)-1-[3-(4-Fluoro-phenyl)-7-hydroxy-8-methyl-8-aza-bicyclo[3.2.1]oct-2-en-2-yl]-propan-1-one O-methyl-oxime
(1'R)-1-[7-Hydroxy-3-(4-iodo-phenyl)-8-methyl-8-aza-bicyclo[3.2.1]oct-2-en-2-yl]-propan-1-one O-methyl-oxime
(1'R)-1-[3-(3,4-Dichloro-phenyl)-7-hydroxy-8-methyl-8-aza-bicyclo[3.2.1]oct-2-en-2-yl]-propan-1-one O-methyl-oxime
(1'R)-Acetic acid 2-acetoxy-4-[7-hydroxy-2-(1-methoxyimino-propyl)-8-methyl-8-aza-bicyclo[3.2.1]oct-2-en-yl]-phenyl ester
(1'R)-1-(7-Hydroxy-8-methyl-3-naphthalen-2-yl-8-aza-bicyclo[3.2.1]oct-2-en-yl)-propan-1-one O-methyl-oxime
(1'S)-1-[3-(4-Fluoro-phenyl)-7-hydroxy-8-methyl-8-aza-bicyclo[3.2.1]oct-2-en-2-yl]-propan-1-one O-methyl-oxime
(1'S)-1-[7-Hydroxy-3-(4-iodo-phenyl)-8-methyl-8-aza-bicyclo[3.2.1]oct-2-en-yl]-propan-1-one O-methyl-oxime
(1'S)-1-[3-(3,4-Dichloro-phenyl)-7-hydroxy-8-methyl-8-aza-bicyclo[3.2.1]oct-2-en-2-yl]-propan-1-one O-methyl-oxime
(1'S)-Acetic acid 2-acetoxy-4-[7-hydroxy-2-(1-methoxyimino-propyl)-8-methyl-8-aza-bicyclo[3.2.1]oct-2-en-yl]-phenyl ester
(1'S)-1-(7-Hydroxy-8-methyl-3-naphthalen-2-yl-8-aza-bicyclo[3.2.1]oct-2-en-yl)-propan-1-one O-methyl-oxime
(1'R)-1-[3-(4-Fluoro-phenyl)-7-hydroxy-8-aza-bicyclo[3.2.1]oct-2-en-2-yl]-propan-1-one O-methyl-oxime
(1'R)-1-[7-Hydroxy-3-(4-iodo-phenyl)-8-aza-bicyclo[3.2.1]oct-2-en-yl]-propan-1-one O-methyl-oxime
(1'R)-1-[3-(3,4-Dichloro-phenyl)-7-hydroxy-8-aza-bicyclo[3.2.1]oct-2-en-2-yl]-propan-1-one O-methyl-oxime
(1'R)-Acetic acid 2-acetoxy-4-[7-hydroxy-2-(1-methoxyimino-propyl)-8-aza-bicyclo[3.2.1]oct-2-en-yl]-phenyl ester
(1'R)-1-(7-Hydroxy-3-naphthalen-2-yl-8-aza-bicyclo[3.2.1]oct-2-en-yl)-propan-1-one O-methyl-oxime
(1'S)-1-[3-(4-Fluoro-phenyl)-7-hydroxy-8-aza-bicyclo[3.2.1]oct-2-en-2-yl]-propan-1-one O-methyl-oxime
(1'S)-1-[7-Hydroxy-3-(4-iodo-phenyl)-8-aza-bicyclo[3.2.1]oct-2-en-yl]-propan-1-one O-methyl-oxime
(1'S)-1-[3-(3,4-Dichloro-phenyl)-7-hydroxy-8-aza-bicyclo[3.2.1]oct-2-en-2-yl]-propan-1-one O-methyl-oxime
(1'S)-Acetic acid 2-acetoxy-4-[7-hydroxy-2-(1-methoxyimino-propyl)-8-aza-bicyclo[3.2.1]oct-2-en-yl]-phenyl ester
(1'S)-1-(7-Hydroxy-3-naphthalen-2-yl-8-aza-bicyclo[3.2.1]oct-2-en-yl)-propan-1-one O-methyl-oxime
(1'R)-1-[3β-(4-Fluoro-phenyl)-7-hydroxy-bicyclo[3.2.1]oct-2β-yl]-propan-1-one O-methyl-oxime
(1'R)-1-[7-Hydroxy-3β-(4-iodo-phenyl)-bicyclo[3.2.1]oct-2β-yl]-propan-1-one O-methyl-oxime
(1'R)-1-[3β-(3,4-Dichloro-phenyl)-7-hydroxy-bicyclo[3.2.1]oct-2β-yl]-propan-1-one O-methyl-oxime
(1'R)-Acetic acid 2-acetoxy-4-[7-hydroxy-2β-(1-methoxyimino-propyl)-bicyclo[3.2.1]oct-3β-yl]-phenyl ester
(1'R)-1-(7-Hydroxy-3β-naphthalen-2-yl-bicyclo[3.2.1]oct-2β-yl)-propan-1-one O-methyl-oxime
(1'R)-1-{3α-[Bis-(4-fluoro-phenyl)-methoxy]-7-hydroxy-bicyclo[3.2.1]oct-2β-yl}-propan-1-one O-methyl-oxime
(1'S)-1-[3β-(4-Fluoro-phenyl)-7-hydroxy-bicyclo[3.2.1]oct-2β-yl]-propan-1-one O-methyl-oxime
(1'S)-1-[7-Hydroxy-3β-(4-iodo-phenyl)-bicyclo[3.2.1]oct-2β-yl]-propan-1-one O-methyl-oxime
(1'S)-1-[3β-(3,4-Dichloro-phenyl)-7-hydroxy-bicyclo[3.2.1]oct-2β-yl]-propan-1-one O-methyl-oxime
(1'S)-Acetic acid 2-acetoxy-4-[7-hydroxy-2β-(1-methoxyimino-propyl)-bicyclo[3.2.1]oct-3β-yl]-phenyl ester
(1'S)-1-(7-Hydroxy-3β-naphthalen-2-yl-bicyclo[3.2.1]oct-2β-yl)-propan-1-one O-methyl-oxime
(1'S)-1-{3α-[Bis-(4-fluoro-phenyl)-methoxy]-7-hydroxy-bicyclo[3.2.1]oct-2β-yl}-propan-1-one O-methyl-oxime
(1'R)-1-[3α-(4-Fluoro-phenyl)-7-hydroxy-bicyclo[3.2.1]oct-2β-yl]-propan-1-one O-methyl-oxime
(1'R)-1-[7-Hydroxy-3α-(4-iodo-phenyl)-bicyclo[3.2.1]oct-2β-yl]-propan-1-one O-methyl-oxime
(1'R)-1-[3α-(3,4-Dichloro-phenyl)-7-hydroxy-bicyclo[3.2.1]oct-2β-yl]-propan-1-one O-methyl-oxime
(1'R)-Acetic acid 2-acetoxy-4-[7-hydroxy-2β-(1-methoxyimino-propyl)-bicyclo[3.2.1]oct-3α-yl]-phenyl ester
(1'R)-1-(7-Hydroxy-3α-naphthalen-2-yl-bicyclo[3.2.1]oct-2β-yl)-propan-1-one O-methyl-oxime
(1'S)-1-[3α-(4-Fluoro-phenyl)-7-hydroxy-bicyclo[3.2.1]oct-2β-yl]-propan-1-one O-methyl-oxime
(1'S)-1-[7-Hydroxy-3α-(4-iodo-phenyl)-bicyclo[3.2.1]oct-2β-yl]-propan-1-one O-methyl-oxime
(1'S)-1-[3α-(3,4-Dichloro-phenyl)-7-hydroxy-bicyclo[3.2.1]oct-2β-yl]-propan-1-one O-methyl-oxime

TABLE 9-continued (1'S)-Acetic acid 2-acetoxy-4-[7-hydroxy-2β-(1-methoxyimino-propyl)-bicyclo[3.2.1]oct-3α-yl]-phenyl ester
(1'S)-1-(7-Hydroxy-3α-naphthalen-2-yl-bicyclo[3.2.1]oct-2β-yl)-propan-1-one O-methyl-oxime
(1'R)-1-[3-(4-Fluoro-phenyl)-7-hydroxy-bicyclo[3.2.1]oct-2-en-2-yl]-propan-1-one O-methyl-oxime
(1'R)-1-[7-Hydroxy-3-(4-iodo-phenyl)-bicyclo[3.2.1]oct-2-en-2-yl]-propan-1-one O-methyl-oxime
(1'R)-1-[3-(3,4-Dichloro-phenyl)-7-hydroxy-bicyclo[3.2.1]oct-2-en-2-yl]-propan-1-one O-methyl-oxime
(1'R)-Acetic acid 2-acetoxy-4-[7-hydroxy-2-(1-methoxyimino-propyl)-bicyclo[3.2.1]oct-2-en-3-yl]-phenyl ester
(1'R)-1-(7-Hydroxy-3-naphthalen-2-yl-bicyclo[3.2.1]oct-2-en-2-yl)-propan-1-one O-methyl-oxime
(1'S)-1-[3-(4-Fluoro-phenyl)-7-hydroxy-bicyclo[3.2.1]oct-2-en-2-yl]-propan-1-one O-methyl-oxime
(1'S)-1-[7-Hydroxy-3-(4-iodo-phenyl)-bicyclo[3.2.1]oct-2-en-2-yl]-propan-1-one O-methyl-oxime
(1'S)-1-[3-(3,4-Dichloro-phenyl)-7-hydroxy-bicyclo[3.2.1]oct-2-en-2-yl]-propan-1-one O-methyl-oxime
(1'S)-Acetic acid 2-acetoxy-4-[7-hydroxy-2-(1-methoxyimino-propyl)-bicyclo[3.2.1]oct-2-en-3-yl]-phenyl ester
(1'S)-1-(7-Hydroxy-3-naphthalen-2-yl-bicyclo[3.2.1]oct-2-en-2-yl)-propan-1-one O-methyl-oxime
(1'R)-1-[3β-(4-Fluoro-phenyl)-7-hydroxy-8-oxa-bicyclo[3.2.1]oct-2β-yl]-propan-1-one O-methyl-oxime
(1'R)-1-[7-Hydroxy-3β-(4-iodo-phenyl)-8-oxa-bicyclo[3.2.1]oct-2β-yl]-propan-1-one O-methyl-oxime
(1'R)-1-[3β-(3,4-Dichloro-phenyl)-7-hydroxy-8-oxa-bicyclo[3.2.1]oct-2β-yl]-propan-1-one O-methyl-oxime
(1'R)-Acetic acid 2-acetoxy-4-[7-hydroxy-2β-(1-methoxyimino-propyl)-8-oxa-bicyclo[3.2.1]oct-3β-yl]-phenyl ester
(1'R)-1-(7-Hydroxy-3β-naphthalen-2-yl-8-oxa-bicyclo[3.2.1]oct-2β-yl)-propan-1-one O-methyl-oxime
(1'R)-1-{3α-[Bis-(4-fluoro-phenyl)-methoxy]-7-hydroxy-bicyclo[3.2.1]oct-2β-yl}-propan-1-one O-methyl-oxime
(1'S)-1-[3β-(4-Fluoro-phenyl)-7-hydroxy-8-oxa-bicyclo[3.2.1]oct-2β-yl]-propan-1-one O-methyl-oxime
(1'S)-1-[7-Hydroxy-3β-(4-iodo-phenyl)-8-oxa-bicyclo[3.2.1]oct-2β-yl]-propan-1-one O-methyl-oxime
(1'S)-1-[3β-(3,4-Dichloro-phenyl)-7-hydroxy-8-oxa-bicyclo[3.2.1]oct-2β-yl]-propan-1-one O-methyl-oxime
(1'S)-Acetic acid 2-acetoxy-4-[7-hydroxy-2β-(1-methoxyimino-propyl)-8-oxa-bicyclo[3.2.1]oct-3β-yl]-phenyl ester
(1'S)-1-(7-Hydroxy-3β-naphthalen-2-yl-8-oxa-bicyclo[3.2.1]oct-2β-yl)-propan-1-one O-methyl-oxime
(1'S)-1-{3α-[Bis-(4-fluoro-phenyl)-methoxy]-7-hydroxy-8-oxa-bicyclo[3.2.1]oct-2β-yl}-propan-1-one O-methyl-oxime
(1'R)-1-[3α-(4-Fluoro-phenyl)-7-hydroxy-8-oxa-bicyclo[3.2.1]oct-2β-yl]-propan-1-one O-methyl-oxime
(1'R)-1-[7-Hydroxy-3α-(4-iodo-phenyl)-8-oxa-bicyclo[3.2.1]oct-2β-yl]-propan-1-one O-methyl-oxime
(1'R)-1-[3α-(3,4-Dichloro-phenyl)-7-hydroxy-8-oxa-bicyclo[3.2.1]oct-2β-yl]-propan-1-one O-methyl-oxime
(1'R)-Acetic acid 2-acetoxy-4-[7-hydroxy-2β-(1-methoxyimino-propyl)-8-oxa-bicyclo[3.2.1]oct-3α-yl]-phenyl ester
(1'R)-1-(7-Hydroxy-3α-naphthalen-2-yl-8-oxa-bicyclo[3.2.1]oct-2β-yl)-propan-1-one O-methyl-oxime
(1'S)-1-[3α-(4-Fluoro-phenyl)-7-hydroxy-8-oxa-bicyclo[3.2.1]oct-2β-yl]-propan-1-one O-methyl-oxime
(1'S)-1-[7-Hydroxy-3α-(4-iodo-phenyl)-8-oxa-bicyclo[3.2.1]oct-2β-yl]-propan-1-one O-methyl-oxime
(1'S)-1-[3α-(3,4-Dichloro-phenyl)-7-hydroxy-8-oxa-bicyclo[3.2.1]oct-2β-yl]-propan-1-one O-methyl-oxime
(1'S)-Acetic acid 2-acetoxy-4-[7-hydroxy-2β-(1-methoxyimino-propyl)-8-oxa-bicyclo[3.2.1]oct-3α-yl]-phenyl ester
(1'S)-1-(7-Hydroxy-3α-naphthalen-2-yl-8-oxa-bicyclo[3.2.1]oct-2β-yl)-propan-1-one O-methyl-oxime
(1'R)-1-[3-(4-Fluoro-phenyl)-7-hydroxy-8-oxa-bicyclo[3.2.1]oct-2-en-2-yl]-propan-1-one O-methyl-oxime
(1'R)-1-[7-Hydroxy-3-(4-iodo-phenyl)-8-oxa-bicyclo[3.2.1]oct-2-en-2-yl]-propan-1-one O-methyl-oxime
(1'R)-1-[3-(3,4-Dichloro-phenyl)-7-hydroxy-8-oxa-bicyclo[3.2.1]oct-2-en-2-yl]-propan-1-one O-methyl-oxime
(1'R)-Acetic acid 2-acetoxy-4-[7-hydroxy-2-(1-methoxyimino-propyl)-8-oxa-bicyclo[3.2.1]oct-2-en-3-yl]-phenyl ester
(1'R)-1-(7-Hydroxy-3-naphthalen-2-yl-8-oxa-bicyclo[3.2.1]oct-2-en-2-yl)-propan-1-one O-methyl-oxime
(1'S)-1-[3-(4-Fluoro-phenyl)-7-hydroxy-8-oxa-bicyclo[3.2.1]oct-2-en-2-yl]-propan-1-one O-methyl-oxime
(1'S)-1-[7-Hydroxy-3-(4-iodo-phenyl)-8-oxa-bicyclo[3.2.1]oct-2-en-2-yl]-propan-1-one O-methyl-oxime
(1'S)-1-[3-(3,4-Dichloro-phenyl)-7-hydroxy-8-oxa-bicyclo[3.2.1]oct-2-en-2-yl]-propan-1-one O-methyl-oxime
(1'S)-Acetic acid 2-acetoxy-4-[7-hydroxy-2-(1-methoxyimino-propyl)-8-oxa-bicyclo[3.2.1]oct-2-en-3-yl]-phenyl ester
(1'S)-1-(7-Hydroxy-3-naphthalen-2-yl-8-oxa-bicyclo[3.2.1]oct-2-en-2-yl)-propan-1-one O-methyl-oxime
(1'R)-1-[3β-(4-Fluoro-phenyl)-7-hydroxy-8-thia-bicyclo[3.2.1]oct-2β-yl]-propan-1-one O-methyl-oxime
(1'R)-1-[7-Hydroxy-3β-(4-iodo-phenyl)-8-thia-bicyclo[3.2.1]oct-2β-yl]-propan-1-one O-methyl-oxime
(1'R)-1-[3β-(3,4-Dichloro-phenyl)-7-hydroxy-8-thia-bicyclo[3.2.1]oct-2β-yl]-propan-1-one O-methyl-oxime
(1'R)-Acetic acid 2-acetoxy-4-[7-hydroxy-2β-(1-methoxyimino-propyl)-8-thia-bicyclo[3.2.1]oct-3β-yl]-phenyl ester
(1'R)-1-(7-Hydroxy-8-thia--3β-naphthalen-2-yl-8-thia-bicyclo[3.2.1]oct-2β-yl)-propan-1-one O-methyl-oxime
(1'R)-1-{3α-[Bis-(4-fluoro-phenyl)-methoxy]-7-hydroxy-bicyclo[3.2.1]oct-2β-yl}-propan-1-one O-methyl-oxime
(1'S)-1-[3β-(4-Fluoro-phenyl)-7-hydroxy-8-thia-bicyclo[3.2.1]oct-2β-yl]-propan-1-one O-methyl-oxime
(1'S)-1-[7-Hydroxy-3β-(4-iodo-phenyl)-8-thia-bicyclo[3.2.1]oct-2β-yl]-propan-1-one O-methyl-oxime
(1'S)-1-[3β-(3,4-Dichloro-phenyl)-7-hydroxy-8-thia-bicyclo[3.2.1]oct-2β-yl]-propan-1-one O-methyl-oxime
(1'S)-Acetic acid 2-acetoxy-4-[7-hydroxy-2β-(1-methoxyimino-propyl)-8-thia-bicyclo[3.2.1]oct-3β-yl]-phenyl ester
(1'S)-1-(7-Hydroxy-3β-naphthalen-2-yl-8-thia-bicyclo[3.2.1]oct-2β-yl)-propan-1-one O-methyl-oxime
(1'S)-1-{3α-[Bis-(4-fluoro-phenyl)-methoxy]-7-hydroxy-bicyclo[3.2.1]oct-2β-yl}-propan-1-one O-methyl-oxime
(1'R)-1-[3α-(4-Fluoro-phenyl)-7-hydroxy-8-thia-bicyclo[3.2.1]oct-2β-yl]-propan-1-one O-methyl-oxime
(1'R)-1-[7-Hydroxy-3α-(4-iodo-phenyl)-8-thia-bicyclo[3.2.1]oct-2β-yl]-propan-1-one O-methyl-oxime
(1'R)-1-[3α-(3,4-Dichloro-phenyl)-7-hydroxy-8-thia-bicyclo[3.2.1]oct-2β-yl]-propan-1-one O-methyl-oxime
(1'R)-Acetic acid 2-acetoxy-4-[7-hydroxy-2β-(1-methoxyimino-propyl)-8-thia-bicyclo[3.2.1]oct-3α-yl]-phenyl ester
(1'R)-1-(7-Hydroxy-8-thia--3α-naphthalen-2-yl-8-thia-bicyclo[3.2.1]oct-2β-yl)-propan-1-one O-methyl-oxime
(1'S)-1-[3α-(4-Fluoro-phenyl)-7-hydroxy-8-thia-bicyclo[3.2.1]oct-2β-yl]-propan-1-one O-methyl-oxime
(1'S)-1-[7-Hydroxy-3α-(4-iodo-phenyl)-8-thia-bicyclo[3.2.1]oct-2β-yl]-propan-1-one O-methyl-oxime
(1'S)-1-[3α-(3,4-Dichloro-phenyl)-7-hydroxy-8-thia-bicyclo[3.2.1]oct-2β-yl]-propan-1-one O-methyl-oxime
(1'S)-Acetic acid 2-acetoxy-4-[7-hydroxy-2β-(1-methoxyimino-propyl)-8-thia-bicyclo[3.2.1]oct-3α-yl]-phenyl ester
(1'S)-1-(7-Hydroxy-3α-naphthalen-2-yl-8-thia-bicyclo[3.2.1]oct-2β-yl)-propan-1-one O-methyl-oxime
(1'R)-1-[3-(4-Fluoro-phenyl)-7-hydroxy-8-thia-bicyclo[3.2.1]oct-2-en-2-yl]-propan-1-one O-methyl-oxime
(1'R)-1-[8-thia-7-Hydroxy-3-(4-iodo-phenyl)-8-thia-bicyclo[3.2.1]oct-2-en-2-yl]-propan-1-one O-methyl-oxime
(1'R)-1-[3-(3,4-Dichloro-phenyl)-7-hydroxy-8-thia-bicyclo[3.2.1]oct-2-en-2-yl]-propan-1-one O-methyl-oxime
(1'R)-Acetic acid 2-acetoxy-4-[7-hydroxy-2-(1-methoxyimino-propyl)-8-thia-bicyclo[3.2.1]oct-2-en-3-yl]-phenyl ester
(1'R)-1-(7-Hydroxy-3-(naphthalen-2-yl)-8-thia-bicyclo[3.2.1]oct-2-en-2-yl)-propan-1-one O-methyl-oxime
(1'S)-1-[3-(4-Fluoro-phenyl)-7-hydroxy-8-thia-bicyclo[3.2.1]oct-2-en-2-yl]-propan-1-one O-methyl-oxime
(1'S)-1-[7-Hydroxy-3-(4-iodo-phenyl)-8-thia-bicyclo[3.2.1]oct-2-en-2-yl]-propan-1-one O-methyl-oxime
(1'S)-1-[3-(3,4-Dichloro-phenyl)-7-hydroxy-8-thia-bicyclo[3.2.1]oct-2-en-2-yl]-propan-1-one O-methyl-oxime
(1'S)-Acetic acid 2-acetoxy-4-[7-hydroxy-2-(1-methoxyimino-propyl)-8-thia-bicyclo[3.2.1]oct-2-en-3-yl]-phenyl ester
(1'S)-1-(7-Hydroxy-3-(naphthalen-2-yl)-8-thia-bicyclo[3.2.1]oct-2-en-2-yl)-propan-1-one O-methyl-oxime
(1'R)-1-[3β-(4-Fluoro-phenyl)-bicyclo[3.2.1]oct-2β-yl]-propan-1-one O-methyl-oxime
(1'R)-1-[3β-(4-iodo-phenyl)-bicyclo[3.2.1]oct-2β-yl]-propan-1-one O-methyl-oxime
(1'R)-1-[3β-(3,4-Dichloro-phenyl)-bicyclo[3.2.1]oct-2β-yl]-propan-1-one O-methyl-oxime

TABLE 9-continued (1'R)-Acetic acid 2-acetoxy-4-[2β-(1-methoxyimino-propyl)-bicyclo[3.2.1]oct-3β-yl]-phenyl ester
(1'R)-1-(3β-naphthalen-2-yl-bicyclo[3.2.1]oct-2β-yl)-propan-1-one O-methyl-oxime
(1'R)-1-{3α-[Bis-(4-fluoro-phenyl)-methoxy]-bicyclo[3.2.1]oct-2β-yl}-propan-1-one O-methyl-oxime
(1'S)-1-[3β-(4-Fluoro-phenyl)-bicyclo[3.2.1]oct-2β-yl]-propan-1-one O-methyl-oxime
(1'S)-1-[3β-(4-iodo-phenyl)-bicyclo[3.2.1]oct-2β-yl]-propan-1-one O-methyl-oxime
(1'S)-1-[3β-(3,4-Dichloro-phenyl)-bicyclo[3.2.1]oct-2β-yl]-propan-1-one O-methyl-oxime
(1'S)-Acetic acid 2-acetoxy-4-[2β-(1-methoxyimino-propyl)-bicyclo[3.2.1]oct-3β-yl]-phenyl ester
(1'S)-1-(3β-naphthalen-2-yl-bicyclo[3.2.1]oct-2β-yl)-propan-1-one O-methyl-oxime
(1'S)-1-{3α-[Bis-(4-fluoro-phenyl)-methoxy]-bicyclo[3.2.1]oct-2β-yl}-propan-1-one O-methyl-oxime
(1'R)-1-[3α-(4-Fluoro-phenyl)-bicyclo[3.2.1]oct-2β-yl]-propan-1-one O-methyl-oxime
(1'R)-1-[3α-(4-iodo-phenyl)-bicyclo[3.2.1]oct-2β-yl]-propan-1-one O-methyl-oxime
(1'R)-1-[3α-(3,4-Dichloro-phenyl)-bicyclo[3.2.1]oct-2β-yl]-propan-1-one O-methyl-oxime
(1'R)-Acetic acid 2-acetoxy-4-[2β-(1-methoxyimino-propyl)-bicyclo[3.2.1]oct-3β-yl]-phenyl ester
(1'R)-1-(3α-naphthalen-2-yl-bicyclo[3.2.1]oct-2β-yl)-propan-1-one O-methyl-oxime
(1'R)-1-[3α-(4-Fluoro-phenyl)-bicyclo[3.2.1]oct-2β-yl]-propan-1-one O-methyl-oxime
(1'R)-1-[3α-(4-iodo-phenyl)-bicyclo[3.2.1]oct-2β-yl]-propan-1-one O-methyl-oxime
(1'R)-1-[3α-(3,4-Dichloro-phenyl)-bicyclo[3.2.1]oct-2β-yl]-propan-1-one O-methyl-oxime
(1'R)-Acetic acid 2-acetoxy-4-[2β-(1-methoxyimino-propyl)-bicyclo[3.2.1]oct-3β-yl]-phenyl ester
(1'R)-1-(3α-naphthalen-2-yl-bicyclo[3.2.1]oct-2β-yl)-propan-1-one O-methyl-oxime
(1'R)-1-[3-(4-Fluoro-phenyl)-bicyclo[3.2.1]oct-2-en-2-yl]-propan-1-one O-methyl-oxime
(1'R)-1-[3-(4-iodo-phenyl)-bicyclo[3.2.1]oct-2-en-2-yl]-propan-1-one O-methyl-oxime
(1'R)-1-[3-(3,4-Dichloro-phenyl)-bicyclo[3.2.1]oct-2-en-2-yl]-propan-1-one O-methyl-oxime
(1'R)-Acetic acid 2-acetoxy-4-[2-(1-methoxyimino-propyl)-bicyclo[3.2.1]oct-2-en-3-yl]-phenyl ester
(1'R)-1-(3-naphthalen-2-yl-bicyclo[3.2.1]oct-2-en-2-yl)-propan-1-one O-methyl-oxime
(1'S)-1-[3-(4-Fluoro-phenyl)-bicyclo[3.2.1]oct-2-en-2-yl]-propan-1-one O-methyl-oxime
(1'S)-1-[3-(4-iodo-phenyl)-bicyclo[3.2.1]oct-2-en-2-yl]-propan-1-one O-methyl-oxime
(1'S)-1-[3-(3,4-Dichloro-phenyl)-bicyclo[3.2.1]oct-2-en-2-yl]-propan-1-one O-methyl-oxime
(1'S)-Acetic acid 2-acetoxy-4-[2-(1-methoxyimino-propyl)-bicyclo[3.2.1]oct-2-en-3-yl]-phenyl ester
(1'S)-1-(3-naphthalen-2-yl-bicyclo[3.2.1]oct-2-en-2-yl)-propan-1-one O-methyl-oxime
(1'R)-1-[3β-(4-Fluoro-phenyl)-8-thia-bicyclo[3.2.1]oct-2β-yl]-propan-1-one O-methyl-oxime
(1'R)-1-[3β-(4-iodo-phenyl)-8-thia-bicyclo[3.2.1]oct-2β-yl]-propan-1-one O-methyl-oxime
(1'R)-1-[3β-(3,4-Dichloro-phenyl)-8-thia-bicyclo[3.2.1]oct-2β-yl]-propan-1-one O-methyl-oxime
(1'R)-Acetic acid 2-acetoxy-4-[2β-(1-methoxyimino-propyl)-8-thia-bicyclo[3.2.1]oct-3β-yl]-phenyl ester
(1'R)-1-(8-thia--3β-naphthalen-2-yl-bicyclo[3.2.1]oct-2β-yl)-propan-1-one O-methyl-oxime
(1'R)-1-{3α-[Bis-(4-fluoro-phenyl)-methoxy]-8-thia-bicyclo[3.2.1]oct-2β-yl}-propan-1-one O-methyl-oxime
(1'S)-1-[3β-(4-Fluoro-phenyl)-8-thia-bicyclo[3.2.1]oct-2β-yl]-propan-1-one O-methyl-oxime
(1'S)-1-[3β-(4-iodo-phenyl)-8-thia-bicyclo[3.2.1]oct-2β-yl]-propan-1-one O-methyl-oxime
(1'S)-1-[3β-(3,4-Dichloro-phenyl)-8-thia-bicyclo[3.2.1]oct-2β-yl]-propan-1-one O-methyl-oxime
(1'S)-Acetic acid 2-acetoxy-4-[2β-(1-methoxyimino-propyl)-8-thia-bicyclo[3.2.1]oct-3β-yl]-phenyl ester
(1'S)-1-(3β-naphthalen-2-yl-8-thia-bicyclo[3.2.1]oct-2β-yl)-propan-1-one O-methyl-oxime
(1'S)-1-{3α-[Bis-(4-fluoro-phenyl)-methoxy]-8-thia-bicyclo[3.2.1]oct-2β-yl}-propan-1-one O-methyl-oxime
(1'R)-1-[3α-(4-Fluoro-phenyl)-8-thia-bicyclo[3.2.1]oct-2β-yl]-propan-1-one O-methyl-oxime
(1'R)-1-[3α-(4-iodo-phenyl)-8-thia-bicyclo[3.2.1]oct-2β-yl]-propan-1-one O-methyl-oxime
(1'R)-1-[3α-(3,4-Dichloro-phenyl)-8-thia-bicyclo[3.2.1]oct-2β-yl]-propan-1-one O-methyl-oxime
(1'R)-Acetic acid 2-acetoxy-4-[2β-(1-methoxyimino-propyl)-8-thia-bicyclo[3.2.1]oct-3α-yl]-phenyl ester
(1'R)-1-(8-thia--3α-naphthalen-2-yl-bicyclo[3.2.1]oct-2β-yl)-propan-1-one O-methyl-oxime
(1'S)-1-[3α-(4-Fluoro-phenyl)-8-thia-bicyclo[3.2.1]oct-2β-yl]-propan-1-one O-methyl-oxime
(1'S)-1-[3α-(4-iodo-phenyl)-8-thia-bicyclo[3.2.1]oct-2β-yl]-propan-1-one O-methyl-oxime
(1'S)-1-[3α-(3,4-Dichloro-phenyl)-8-thia-bicyclo[3.2.1]oct-2β-yl]-propan-1-one O-methyl-oxime
(1'S)-Acetic acid 2-acetoxy-4-[2β-(1-methoxyimino-propyl)-8-thia-bicyclo[3.2.1]oct-3α-yl]-phenyl ester
(1'S)-1-(3α-(naphthalen-2-yl)-8-thia-bicyclo[3.2.1]oct-2β-yl)-propan-1-one O-methyl-oxime
(1'R)-1-[3-(4-Fluoro-phenyl)-8-thia-bicyclo[3.2.1]oct-2-en-2-yl]-propan-1-one O-methyl-oxime
(1'R)-1-[8-thia-3-(4-iodo-phenyl)-8-thia-bicyclo[3.2.1]oct-2-en-2-yl]-propan-1-one O-methyl-oxime
(1'R)-1-[3-(3,4-Dichloro-phenyl)-8-thia-bicyclo[3.2.1]oct-2-en-2-yl]-propan-1-one O-methyl-oxime
(1'R)-Acetic acid 2-acetoxy-4-[2-(1-methoxyimino-propyl)-8-thia-bicyclo[3.2.1]oct-2-en-3-yl]-phenyl ester
(1'R)-1-(3-(naphthalen-2-yl)-8-thia-bicyclo[3.2.1]oct-2-en-2-yl)-propan-1-one O-methyl-oxime
(1'S)-1-[3-(4-Fluoro-phenyl)-8-thia-bicyclo[3.2.1]oct-2-en-2-yl]-propan-1-one O-methyl-oxime
(1'S)-1-[3-(4-iodo-phenyl)-8-thia-bicyclo[3.2.1]oct-2-en-2-yl]-propan-1-one O-methyl-oxime
(1'S)-1-[3-(3,4-Dichloro-phenyl)-8-thia-bicyclo[3.2.1]oct-2-en-2-yl]-propan-1-one O-methyl-oxime
(1'S)-Acetic acid 2-acetoxy-4-[2-(1-methoxyimino-propyl)-8-thia-bicyclo[3.2.1]oct-2-en-3-yl]-phenyl ester
(1'S)-1-(3-(naphthalen-2-yl)-8-thia-bicyclo[3.2.1]oct-2-en-2-yl)-propan-1-one O-methyl-oxime
(1'R)-1-[3β-(4-Fluoro-phenyl)-8-methyl-8-aza-bicyclo[3.2.1]oct-2β-yl]-propan-1-one O-methyl-oxime
(1'R)-1-[3β-(4-iodo-phenyl)-8-methyl-8-aza-bicyclo[3.2.1]oct-2β-yl]-propan-1-one O-methyl-oxime
(1'R)-1-[3β-(3,4-Dichloro-phenyl)-8-methyl-8-aza-bicyclo[3.2.1]oct-2β-yl]-propan-1-one O-methyl-oxime
(1'R)-Acetic acid 2-acetoxy-4-[2β-(1-methoxyimino-propyl)-8-methyl-8-aza-bicyclo[3.2.1]oct-3β-yl]-phenyl ester
(1'R)-1-(8-methyl-3β-naphthalen-2-yl-8-aza-bicyclo[3.2.1]oct-2β-yl)-propan-1-one O-methyl-oxime
(1'R)-1-{3α-[Bis-(4-fluoro-phenyl)-methoxy]-8-methyl-8-aza-bicyclo[3.2.1]oct-2β-yl}-propan-1-one O-methyl-oxime
(1'S)-1-[3β-(4-Fluoro-phenyl)-8-methyl-8-aza-bicyclo[3.2.1]oct-2β-yl]-propan-1-one O-methyl-oxime
(1'S)-1-[3β-(4-iodo-phenyl)-8-methyl-8-aza-bicyclo[3.2.1]oct-2β-yl]-propan-1-one O-methyl-oxime
(1'S)-1-[3β-(3,4-Dichloro-phenyl)-8-methyl-8-aza-bicyclo[3.2.1]oct-2β-yl]-propan-1-one O-methyl-oxime
(1'S)-Acetic acid 2-acetoxy-4-[2β-(1-methoxyimino-propyl)-8-methyl-8-aza-bicyclo[3.2.1]oct-3β-yl]-phenyl ester
(1'S)-1-(8-methyl-3β-naphthalen-2-yl-8-aza-bicyclo[3.2.1]oct-2β-yl)-propan-1-one O-methyl-oxime
(1'S)-1-{3α-[Bis-(4-fluoro-phenyl)-methoxy]-8-methyl-8-aza-bicyclo[3.2.1]oct-2β-yl}-propan-1-one O-methyl-oxime
(1'R)-1-[3α-(4-Fluoro-phenyl)-8-methyl-8-aza-bicyclo[3.2.1]oct-2β-yl]-propan-1-one O-methyl-oxime
(1'R)-1-[3α-(4-iodo-phenyl)-8-methyl-8-aza-bicyclo[3.2.1]oct-2β-yl]-propan-1-one O-methyl-oxime
(1'R)-1-[3α-(3,4-Dichloro-phenyl)-8-methyl-8-aza-bicyclo[3.2.1]oct-2β-yl]-propan-1-one O-methyl-oxime
(1'R)-Acetic acid 2-acetoxy-4-[2β-(1-methoxyimino-propyl)-8-methyl-8-aza-bicyclo[3.2.1]oct-3α-yl]-phenyl ester
(1'R)-1-(8-methyl-3α-naphthalen-2-yl-8-aza-bicyclo[3.2.1]oct-2β-yl)-propan-1-one O-methyl-oxime
(1'S)-1-[3α-(4-Fluoro-phenyl)-8-methyl-8-aza-bicyclo[3.2.1]oct-2β-yl]-propan-1-one O-methyl-oxime TABLE 9-continued (1'S)-1-[3α-(4-iodo-phenyl)-8-methyl-8-aza-bicyclo[3.2.1]oct-2β-yl]-propan-1-one O-methyl-oxime
(1'S)-1-[3α-(3,4-Dichloro-phenyl)-8-methyl-8-aza-bicyclo[3.2.1]oct-2β-yl]-propan-1-one O-methyl-oxime
(1'S)-Acetic acid 2-acetoxy-4-[2β-(1-methoxyimino-propyl)-8-methyl-8-aza-bicyclo[3.2.1]oct-3α-yl]-phenyl ester
(1'S)-1-(8-methyl-3α-naphthalen-2-yl-8-aza-bicyclo[3.2.1]oct-2β-yl)-propan-1-one O-methyl-oxime
(1'R)-1-[3β-(4-Fluoro-phenyl)-8-aza-bicyclo[3.2.1]oct-2β-yl]-propan-1-one O-methyl-oxime
(1'R)-1-[3β-(4-iodo-phenyl)-8-aza-bicyclo[3.2.1]oct-2β-yl]-propan-1-one O-methyl-oxime
(1'R)-1-[3β-(3,4-Dichloro-phenyl)-8-aza-bicyclo[3.2.1]oct-2β-yl]-propan-1-one O-methyl-oxime
(1'R)-Acetic acid 2-acetoxy-4-[2β-(1-methoxyimino-propyl)-8-aza-bicyclo[3.2.1]oct-3β-yl]-phenyl ester
(1'R)-1-(3β-naphthalen-2-yl-8-aza-bicyclo[3.2.1]oct-2β-yl)-propan-1-one O-methyl-oxime
(1'R)-1-{3α-[Bis-(4-fluoro-phenyl)-methoxy]-8-aza-bicyclo[3.2.1]oct-2β-yl}-propan-1-one O-methyl-oxime
(1'S)-1-[3β-(4-Fluoro-phenyl)-8-aza-bicyclo[3.2.1]oct-2β-yl]-propan-1-one O-methyl-oxime
(1'S)-1-[3β-(4-iodo-phenyl)-8-aza-bicyclo[3.2.1]oct-2β-yl]-propan-1-one O-methyl-oxime
(1'S)-1-[3β-(3,4-Dichloro-phenyl)-8-aza-bicyclo[3.2.1]oct-2β-yl]-propan-1-one O-methyl-oxime
(1'S)-Acetic acid 2-acetoxy-4-[2β-(1-methoxyimino-propyl)-8-aza-bicyclo[3.2.1]oct-3β-yl]-phenyl ester
(1'S)-1-(3β-naphthalen-2-yl-8-aza-bicyclo[3.2.1]oct-2β-yl)-propan-1-one O-methyl-oxime
(1'S)-1-{3α-[Bis-(4-fluoro-phenyl)-methoxy]-8-aza-bicyclo[3.2.1]oct-2β-yl}-propan-1-one O-methyl-oxime
(1'R)-1-[3α-(4-Fluoro-phenyl)-8-aza-bicyclo[3.2.1]oct-2β-yl]-propan-1-one O-methyl-oxime
(1'R)-1-[3α-(4-iodo-phenyl)-8-aza-bicyclo[3.2.1]oct-2β-yl]-propan-1-one O-methyl-oxime
(1'R)-1-[3α-(3,4-Dichloro-phenyl)-8-aza-bicyclo[3.2.1]oct-2β-yl]-propan-1-one O-methyl-oxime
(1'R)-Acetic acid 2-acetoxy-4-[2β-(1-methoxyimino-propyl)-8-aza-bicyclo[3.2.1]oct-3α-yl]-phenyl ester
(1'R)-1-(3α-naphthalen-2-yl-8-aza-bicyclo[3.2.1]oct-2β-yl)-propan-1-one O-methyl-oxime
(1'S)-1-[3α-(4-Fluoro-phenyl)-8-aza-bicyclo[3.2.1]oct-2β-yl]-propan-1-one O-methyl-oxime
(1'S)-1-[3α-(4-iodo-phenyl)-8-aza-bicyclo[3.2.1]oct-2β-yl]-propan-1-one O-methyl-oxime
(1'S)-1-[3α-(3,4-Dichloro-phenyl)-8-aza-bicyclo[3.2.1]oct-2β-yl]-propan-1-one O-methyl-oxime
(1'S)-Acetic acid 2-acetoxy-4-[2β-(1-methoxyimino-propyl)-8-aza-bicyclo[3.2.1]oct-3α-yl]-phenyl ester
(1'S)-1-(3α-naphthalen-2-yl-8-aza-bicyclo[3.2.1]oct-2β-yl)-propan-1-one O-methyl-oxime
(1'R)-1-[3-(4-Fluoro-phenyl)-8-methyl-8-aza-bicyclo[3.2.1]oct-2-en-2-yl]-propan-1-one O-methyl-oxime
(1'R)-1-[3-(4-iodo-phenyl)-8-methyl-8-aza-bicyclo[3.2.1]oct-2-en-2-yl]-propan-1-one O-methyl-oxime
(1'R)-1-[3-(3,4-Dichloro-phenyl)-8-methyl-8-aza-bicyclo[3.2.1]oct-2-en-2-yl]-propan-1-one O-methyl-oxime
(1'R)-Acetic acid 2-acetoxy-4-[2-(1-methoxyimino-propyl)-8-methyl-8-aza-bicyclo[3.2.1]oct-2-en-3-yl]-phenyl ester
(1'R)-1-(8-methyl-3-naphthalen-2-yl-8-aza-bicyclo[3.2.1]oct-2-en-2-yl)-propan-1-one O-methyl-oxime
(1'S)-1-[3-(4-Fluoro-phenyl)-8-methyl-8-aza-bicyclo[3.2.1]oct-2-en-2-yl]-propan-1-one O-methyl-oxime
(1'S)-1-[3-(4-iodo-phenyl)-8-methyl-8-aza-bicyclo[3.2.1]oct-2-en-2-yl]-propan-1-one O-methyl-oxime
(1'S)-1-[3-(3,4-Dichloro-phenyl)-8-methyl-8-aza-bicyclo[3.2.1]oct-2-en-2-yl]-propan-1-one O-methyl-oxime
(1'S)-Acetic acid 2-acetoxy-4-[2-(1-methoxyimino-propyl)-8-methyl-8-aza-bicyclo[3.2.1]oct-2-en-3-yl]-phenyl ester
(1'S)-1-(8-methyl-3-naphthalen-2-yl-8-aza-bicyclo[3.2.1]oct-2-en-2-yl)-propan-1-one O-methyl-oxime
(1'R)-1-[3-(4-Fluoro-phenyl)-8-aza-bicyclo[3.2.1]oct-2-en-2-yl]-propan-1-one O-methyl-oxime
(1'R)-1-[3-(4-iodo-phenyl)-8-aza-bicyclo[3.2.1]oct-2-en-2-yl]-propan-1-one O-methyl-oxime
(1'R)-1-[3-(3,4-Dichloro-phenyl)-8-aza-bicyclo[3.2.1]oct-2-en-2-yl]-propan-1-one O-methyl-oxime
(1'R)-Acetic acid 2-acetoxy-4-[2-(1-methoxyimino-propyl)-8-aza-bicyclo[3.2.1]oct-2-en-3-yl]-phenyl ester
(1'R)-1-(3-naphthalen-2-yl-8-aza-bicyclo[3.2.1]oct-2-en-2-yl)-propan-1-one O-methyl-oxime
(1'S)-1-[3-(4-Fluoro-phenyl)-7-8-aza-bicyclo[3.2.1]oct-2-en-2-yl]-propan-1-one O-methyl-oxime
(1'S)-1-[3-(4-iodo-phenyl)-8-aza-bicyclo[3.2.1]oct-2-en-2-yl]-propan-1-one O-methyl-oxime
(1'S)-1-[3-(3,4-Dichloro-phenyl)-8-aza-bicyclo[3.2.1]oct-2-en-2-yl]-propan-1-one O-methyl-oxime
(1'S)-Acetic acid 2-acetoxy-4-[2-(1-methoxyimino-propyl)-8-aza-bicyclo[3.2.1]oct-2-en-3-yl]-phenyl ester
(1'S)-1-(3-naphthalen-2-yl-8-aza-bicyclo[3.2.1]oct-2-en-2-yl)-propan-1-one O-methyl-oxime
(1'R)-1-[3β-(4-Fluoro-phenyl)-8-oxa-bicyclo[3.2.1]oct-2β-yl]-propan-1-one O-methyl-oxime
(1'R)-1-[3β-(4-iodo-phenyl)-8-oxa-bicyclo[3.2.1]oct-2β-yl]-propan-1-one O-methyl-oxime
(1'R)-1-[3β-(3,4-Dichloro-phenyl)-8-oxa-bicyclo[3.2.1]oct-2β-yl]-propan-1-one O-methyl-oxime
(1'R)-Acetic acid 2-acetoxy-4-[2β-(1-methoxyimino-propyl)-8-oxa-bicyclo[3.2.1]oct-3β-yl]-phenyl ester
(1'R)-1-(3β-naphthalen-2-yl-8-oxa-bicyclo[3.2.1]oct-2β-yl)-propan-1-one O-methyl-oxime
(1'R)-1-{3α-[Bis-(4-fluoro-phenyl)-methoxy]-8-oxa-bicyclo[3.2.1]oct-2β-yl}-propan-1-one O-methyl-oxime
(1'S)-1-[3β-(4-Fluoro-phenyl)-8-oxa-bicyclo[3.2.1]oct-2β-yl]-propan-1-one O-methyl-oxime
(1'S)-1-[3β-(4-iodo-phenyl)-8-oxa-bicyclo[3.2.1]oct-2β-yl]-propan-1-one O-methyl-oxime
(1'S)-1-[3β-(3,4-Dichloro-phenyl)-8-oxa-bicyclo[3.2.1]oct-2β-yl]-propan-1-one O-methyl-oxime
(1'S)-Acetic acid 2-acetoxy-4-[2β-(1-methoxyimino-propyl)-8-oxa-bicyclo[3.2.1]oct-3β-yl]-phenyl ester
(1'S)-1-(3β-naphthalen-2-yl-8-oxa-bicyclo[3.2.1]oct-2β-yl)-propan-1-one O-methyl-oxime
(1'S)-1-{3α-[Bis-(4-fluoro-phenyl)-methoxy]-8-oxa-bicyclo[3.2.1]oct-2β-yl}-propan-1-one O-methyl-oxime
(1'R)-1-[3α-(4-Fluoro-phenyl)-8-oxa-bicyclo[3.2.1]oct-2β-yl]-propan-1-one O-methyl-oxime
(1'R)-1-[3α-(4-iodo-phenyl)-8-oxa-bicyclo[3.2.1]oct-2β-yl]-propan-1-one O-methyl-oxime
(1'R)-1-[3α-(3,4-Dichloro-phenyl)-8-oxa-bicyclo[3.2.1]oct-2β-yl]-propan-1-one O-methyl-oxime
(1'R)-Acetic acid 2-acetoxy-4-[2β-(1-methoxyimino-propyl)-8-oxa-bicyclo[3.2.1]oct-3α-yl]-phenyl ester
(1'R)-1-(3α-naphthalen-2-yl-8-oxa-bicyclo[3.2.1]oct-2β-yl)-propan-1-one O-methyl-oxime
(1'S)-1-[3α-(4-Fluoro-phenyl)-8-oxa-bicyclo[3.2.1]oct-2β-yl]-propan-1-one O-methyl-oxime
(1'S)-1-[3α-(4-iodo-phenyl)-8-oxa-bicyclo[3.2.1]oct-2β-yl]-propan-1-one O-methyl-oxime
(1'S)-1-[3α-(3,4-Dichloro-phenyl)-8-oxa-bicyclo[3.2.1]oct-2β-yl]-propan-1-one O-methyl-oxime
(1'S)-Acetic acid 2-acetoxy-4-[2β-(1-methoxyimino-propyl)-8-oxa-bicyclo[3.2.1]oct-3α-yl]-phenyl ester
(1'S)-1-(3α-naphthalen-2-yl-8-oxa-bicyclo[3.2.1]oct-2β-yl)-propan-1-one O-methyl-oxime
(1'R)-1-[3-(4-Fluoro-phenyl)-8-oxa-bicyclo[3.2.1]oct-2-en-2-yl]-propan-1-one O-methyl-oxime
(1'R)-1-[3-(4-iodo-phenyl)-8-oxa-bicyclo[3.2.1]oct-2-en-2-yl]-propan-1-one O-methyl-oxime
(1'R)-1-[3-(3,4-Dichloro-phenyl)-8-oxa-bicyclo[3.2.1]oct-2-en-2-yl]-propan-1-one O-methyl-oxime
(1'R)-Acetic acid 2-acetoxy-4-[2-(1-methoxyimino-propyl)-8-oxa-bicyclo[3.2.1]oct-2-en-3-yl]-phenyl ester
(1'R)-1-(3-naphthalen-2-yl-8-oxa-bicyclo[3.2.1]oct-2-en-2-yl)-propan-1-one O-methyl-oxime
(1'S)-1-[3-(4-Fluoro-phenyl)-8-oxa-bicyclo[3.2.1]oct-2-en-2-yl]-propan-1-one O-methyl-oxime
(1'S)-1-[3-(4-iodo-phenyl)-8-oxa-bicyclo[3.2.1]oct-2-en-2-yl]-propan-1-one O-methyl-oxime
(1'S)-1-[3-(3,4-Dichloro-phenyl)-8-oxa-bicyclo[3.2.1]oct-2-en-2-yl]-propan-1-one O-methyl-oxime
(1'S)-Acetic acid 2-acetoxy-4-[2-(1-methoxyimino-propyl)-8-oxa-bicyclo[3.2.1]oct-2-en-3-yl]-phenyl ester
(1'S)-1-(3-naphthalen-2-yl-8-oxa-bicyclo[3.2.1]oct-2-en-2-yl)-propan-1-one O-methyl-oxime The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

We claim:

1. A compound having the formula:

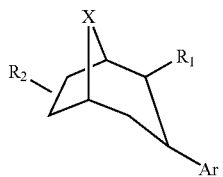

Formula VI

Where:
- the 2-, 3-, 6-, or 7- positions are α or β;
- the compounds are racemic or 1R- or 1S- configured;
- X=O, $NR_3$, $NR_{10}$, N-L-Ch, $CHR_3$, $CHR_1$, $CH_2$,$CHW_1$, $CW_1W_1$, CO, S, SO, $SO_2$, $NSO_2R_3$, $NSO_2R_{11}$ or $CX_2W$, with the N, C, O or S atom being a member of the ring;
- L is a linking moiety comprising a chain of atoms containing 2 to about 6 carbon atoms;
- Ch is a tridentate or tetradentate chelating ligand that forms a neutral complex with technetium or rhenium;
- Ar=Phenyl or 1-naphthyl or 2-naphthyl, unsubstituted or substituted with one or more group selected from: —H; —Br; —Cl; —I; —F; —OH; —$CH_3$; —$OCH_3$; —$CF_3$; —$NO_2$; —$NH_2$; —CN; —$NHCOCH_3$, —$C(CH_3)_3$, —$C(CH_2)CH_3$, $(CH_2)_qCH_3$, where q=0-6; —$COCH_3$; OAc; alkyl; alkenyl; alkynyl; allyl; isopropyl; isobutyl; wherein each substitutent can be at the 2, 3 and/or 4 position of the ring;
- W or $X_2$=H, OH, $OCH_3$, OAc, $OCOR_4$, $CH_3$, $(CH_2)_nCH_3$, $R_4$;
- $W_1$=H, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$;
- $R_3$=independently for each occurrence H, $CH_3$, $CH_2Ar$, $(CH_2)_nAr$, Ar, alkyl, alkenyl or alkynyl, cycloalkylmethyl, $CH_2CH=CHZ$, $(CH_2)_nOH$, $(CH_2)_nOR_4$, CH=CHZ; $CH_2$J-Maleimide, $CH_2$JN-Maleimide where J=$CH_2$ or O; $(CH_2)_nOCOCH_3$; $(CH_2)_nOCOCH_2OCH_3$; $(CH_2)_n$-morpholine; $(CH_2)_n$-piperidine; $(CH_2)_n$-piperazine;
- $R_4$=$CH_3$, $CH_2CH_3$, alkyl, alkenyl, alkynyl, allyl, isopropyl, isobutyl;
- $R_5$=H, $CH_3$, $(CH_3)_2$, $(CH_2)_nSO_3Q$, alkyl, (alkyl)$_2$, alkenyl, alkynyl, Ar, $OCH_3$;
- Q=$K^+$, $Na^+$, $Li^+$, $Ca^{2+}$, $NH_4^+$, $RNH_3^+$, or other pharmaceutically acceptable salts;
- $R_{10}$=$COR_4$, $CH_2OH$, $(CH_2)_nOH$, $(CH_2)_nOR_4$, $(CH_2)_nCOOR_3$, $(CH_2)_nOCOR_3$;
- $R_2$=$R_3$, $OR_3$, isopropyl, isobutyl, $OCOR_4$, $OCOR_5$, $W_1$, $CH_2R_3$, $OCOR_3$, $NHR_3$, $COR_3$, $(CH_2)_nCOOR_3$;
- $R_1$=H, $(CH_2)_nOH$, $(CH_2)_nOR_4$, $CR_3$=$NOR_3$, CH=$NR_3$; $COOR_8$, $COR_8$, $CONHR_8$, $CONR_8R_8$, $CH_2CH_3$, $(CH_2)_nCH_3$, $CHCHR_9$, $(CH_2)_nCCR_9$, $(CH_2)_nCOOR_8$, $(CH_2)_nOCOR_8$, $OCOR_8$, $C_3HNOR_9$ or $C_2N_2OR_9$;
- $R_8$=$R_3$, Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$; $C(CH_3)_3$, $C_{10}H_7$ or $C_{10}H_6W_1$;
- $R_9$=$COOR_8$, $CH_3$, $(CH_2)_nCH_3$, $C_6H_5$, $C_6H_4Y$, $C_{10}H_7$ or $C_{10}H_6W_1$;
- n=0-4;
- m=0-4; and
- Z=F, Cl, I or Br;

wherein at least one of X, $R_2$ or $R_1$ comprises a $COOR_3$ group or a $OCOR_3$ group and wherein at least one $R_3$ group comprises an alkyl, cycloalkylmethyl, alkenyl or alkynyl group, said alkyl, cycloalkylmethyl, alkenyl or alkynyl group having from 10 to 20 carbon atoms.

2. The compound of claim 1, wherein the $R_2$ substituent comprises the $R_3$ alkyl, cycloalkylmethyl, alkenyl or alkynyl group having from 10 to 20 carbon atoms.

3. A pharmaceutical composition comprising a pharmaceutically acceptable carrier and a therapeutically effective amount of a compound according to claim 1.

4. A method of diagnosing a disease that affects monoamine transport comprising labeling a compound of claim 1, administering the labeled compound to a patient, imaging the binding of the labeled compound in the patient, and comparing said imaged patient binding to a reference standard.

5. The method of claim 4, wherein the reference standard is that of a normal human subject lacking a disease or disorder of the nervous system, such that the imaged patient binding can be determined to be similar or dissimilar to the binding of the normal human subject.

6. The method of claim 5, wherein the method is used to diagnose a disease or disorder affecting the patient.

7. The method of claim 6 in which the disease or disorder is attention deficit hyperactivity disorder (ADHD); Parkinson's disease; cocaine addiction.

* * * * *